(12) United States Patent
Chen et al.

(10) Patent No.: US 8,569,468 B2
(45) Date of Patent: Oct. 29, 2013

(54) NANOPLASMONIC MOLECULAR RULER FOR NUCLEASE ACTIVITY AND DNA FOOTPRINTING

(75) Inventors: Fanqing Frank Chen, Moraga, CA (US); Gang L. Liu, Berkeley, CA (US); Luke P. Lee, Orinda, CA (US)

(73) Assignee: The Regents of the University of California, Oakland, CA (US)

( * ) Notice: Subject to any disclaimer, the term of this patent is extended or adjusted under 35 U.S.C. 154(b) by 788 days.

(21) Appl. No.: 12/440,579

(22) PCT Filed: Sep. 14, 2007

(86) PCT No.: PCT/US2007/020026
§ 371 (c)(1),
(2), (4) Date: Jan. 25, 2010

(87) PCT Pub. No.: WO2008/073175
PCT Pub. Date: Jun. 19, 2008

(65) Prior Publication Data
US 2010/0323906 A1    Dec. 23, 2010

Related U.S. Application Data

(60) Provisional application No. 60/844,991, filed on Sep. 14, 2006.

(51) Int. Cl.
*C12Q 1/68* (2006.01)
(52) U.S. Cl.
USPC .......................... 536/23.1; 977/773; 977/762
(58) Field of Classification Search
None
See application file for complete search history.

(56) References Cited

U.S. PATENT DOCUMENTS

| | | | |
|---|---|---|---|
| 6,579,721 B1 | 6/2003 | Natan et al. | |
| 7,250,499 B2 | 7/2007 | Mirkin et al. | |
| 2003/0092029 A1* | 5/2003 | Josephson et al. | 435/6 |

FOREIGN PATENT DOCUMENTS

| | | |
|---|---|---|
| WO | WO 01/09388 | 2/2001 |
| WO | WO 2005/007887 | 1/2005 |
| WO | WO 2008/073175 | 6/2008 |

OTHER PUBLICATIONS

CN Office Action dated Jul. 3, 2012 issued in CN200780042357.4.
International Search Report dated Aug. 7, 2008 issued in WO/2008/073175 (PCT/US2007/020026).
Sonnichsen et al. "A molecular ruler based on plasmon coupling of single gold and silver nanoparticles" Nature Biotechnology, Jun. 2005, vol. 23, No. 6, pp. 741-745.
International Preliminary Report on Patentability and Written Opinion dated Mar. 17, 2009 issued in WO 2008/073175 (PCT/US2007/020026).
European Extended Search report dated Dec. 1, 2010 issued in EP07870761.9.
EP Office Action dated May 16, 2012 issued in EP07870761.9.
Alivisatos et al. (1996) "Organization of 'nanocrystal molecules' using DNA." *Nature* 382: 609-611.
Doron-Mor et al. (2005) "Sensitivity of Transmission Surface Plasmon Resonance (T-SPR) Spectroscopy: Self-Assembled Multilayers on Evaporated Gold Island Films" *Chem. Eur. J.* 11(19): 5555-5562.
Endo et al. (2005) "Label-free detection of peptide nucleic acid-DNA hybridization using localized surface plasmon resonance based optical biosensor" *Analytical Chemistry* 77(21): 6976-6984.
Foultier et al. (2005) "Comparison of DNA detection methods using nanoparticles and silver enhancement" *Iee Proceedings—Nanobiotechnology* 152(1): 3-12.
Glass et al. (2006) "Enzyme-mediated individual nanoparticle release assay" *Analytical Biochemistry* 353(2): 209-216.
Parak et al. (2003) "Conformation of Oligonucleotides Attached to Gold Nanocrystals Probed by Gel Electrophoresis" *Nano Lett.* 3: 33-36.
Sato et al. (2006) "Surface plasmon resonance imaging on a microchip for detection of DNA-modified gold nanoparticles deposited onto the surface in a non-cross-linking configuration" *Analytical Biochemistry* 355(1): 125-131.
Storhoff et al. (1998) "One-pot colorimetric differentiation of polynucleotides with single base imperfections using gold nanoparticles probes." *J. Am. Chem. Soc.* 120: 1959-1964.
Taton et al. (2000) "Scanometric DNA array detection with nanoparticle probes." *Science* 289: 1757-1760.
Wanunu et al. (2005) "Branched Coordination Multilayers on Gold" *Am. Chem. Soc.* 127(50): 17877-17887.
Zanchet et al. (2001) "Electrophoretic isolation of discrete Au nanocrystal/DNA conjugates." *Nano Lett* 1: 32-35.

* cited by examiner

*Primary Examiner* — Anand Desai
(74) *Attorney, Agent, or Firm* — Tom Hunter; Weaver Austin Villeneuve & Sampson LLP

(57) ABSTRACT

This invention provides a nanoplasmonic molecular ruler, which can perform label-free and real-time monitoring of nucleic acid (e.g., DNA) length changes and perform nucleic acid footprinting. In various embodiments the ruler comprises a nucleic acid attached to a nanoparticle, such that changes in the nucleic acid length are detectable using surface plasmon resonance. The nanoplasmonic ruler provides a fast and convenient platform for mapping nucleic acid-protein interactions, for nuclease activity monitoring, and for other footprinting related methods.

17 Claims, 23 Drawing Sheets

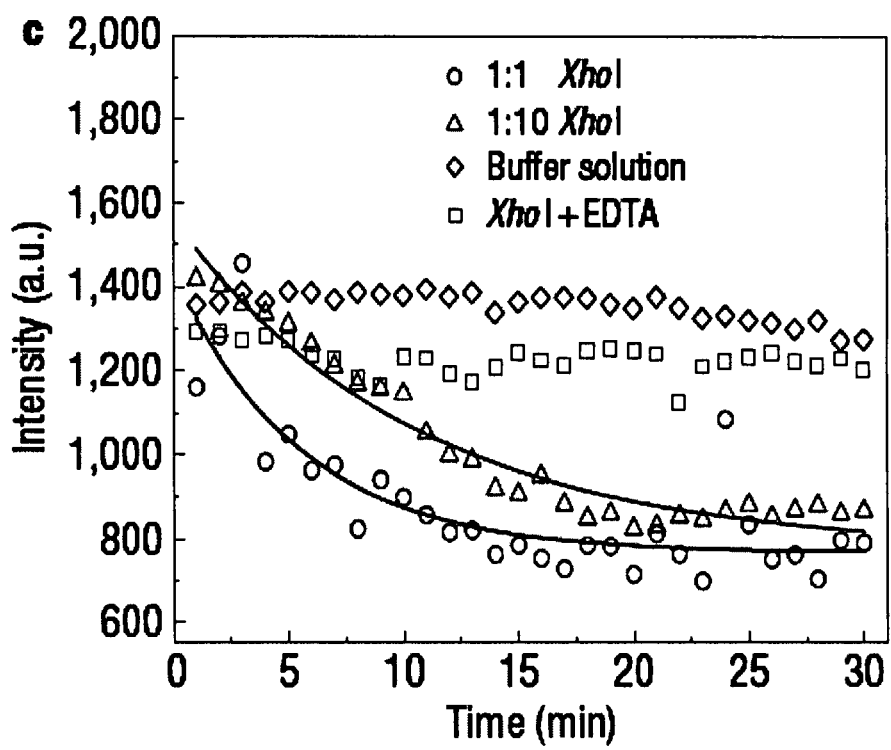
Fig. 3B, cont'd.

*panel a*

*panel b*

```
-S-AAAGGATCCAAGCTTGAATTCCTCGTTTAGCGCGTCGACGATATCGGTACCAAA-3'
   ||||||||||||||||||||||||||||||||||||||||||||||||||||
   TTTCCTAGGTTCGAACTTAAGGAGCAAACCGCGCAGCTGCTATAGCCATGGTTT-5'
```

**TTTGGCGC = binding site for transcriptional factor
E2F1 on CYCD1 gene promoter**

*Fig. 15A*

```
                                    ↓
-S-AAAGGATCCAAGCTTGAATTCCTCGTTTAGCGCGTCGACGATATCGGTACCAAA-3'
   |||||||||||||||||||||||||||||X||||||||||||||||||||||||
   TTTCCTAGGTTCGAACTTAAGGAGCAAACCGCGCAGCTGCTATAGCCATGGTTT-5'
```

A = binding site for DNA mismatch binding protein MutS
(either from E. coli or Taq bacteria or other mismatch
binding proteins)

*Fig. 15B*

```
                                              ↓
-S-AAAGGATCCAAGCTTGAATTCCTCGTTTAGCGCGTC
   |||||||||||||||||||||||||||||X|||||||
   TTTCCTAGGTTCGAACTTAAGGAGCAAACCGCGCAG
```

*Fig. 15C*

```
-S-AAAGGATCCAAGCTTGAATTCCTCGTTTGGCGCGTCGACG
   |||||||||||||||||||||||||||||||||||||||||
     TTTCCTAGGTTCGAACTTAAGGAGCAAACCGCGCAGCTGC
```

TTTGGCGC = binding site for transcriptional factor E2F1 on CYCD1 gene promoter

*Fig. 15D*

```
                              SEQUENCE LISTING

<160> NUMBER OF SEQ ID NOS: 17

<210> SEQ ID NO 1
<211> LENGTH: 54
<212> TYPE: DNA
<213> ORGANISM: Artificial
<220> FEATURE:
<223> OTHER INFORMATION: Synthetic oligonucleotide

<400> SEQUENCE: 1
aaaggatcca agcttgaatt cctcgagaga tctgtcgacg atatcggtac caaa          54

<210> SEQ ID NO 2
<211> LENGTH: 54
<212> TYPE: DNA
<213> ORGANISM: Artificial
<220> FEATURE:
<223> OTHER INFORMATION: Synthetic oligonucleotide

<400> SEQUENCE: 2
tttcctaggt tcgaacttaa ggagctctct agacagctgc tatagccatg gttt          54

<210> SEQ ID NO 3
<211> LENGTH: 54
<212> TYPE: DNA
<213> ORGANISM: Artificial
<220> FEATURE:
<223> OTHER INFORMATION: Synthetic oligonucleotide

<400> SEQUENCE: 3
aaaggatcca agcttgaatt cctcgagaga tctgtcgacg atatcggtac caaa          54

<210> SEQ ID NO 4
<211> LENGTH: 54
<212> TYPE: DNA
<213> ORGANISM: Artificial
<220> FEATURE:
<223> OTHER INFORMATION: Synthetic oligonucleotide

<400> SEQUENCE: 4
tttcctaggt tcgaacttaa ggagctctct agacagctgc tatagccatg gttt          54

<210> SEQ ID NO 5
<211> LENGTH: 28
<212> TYPE: DNA
<213> ORGANISM: Artificial
<220> FEATURE:
<223> OTHER INFORMATION: Synthetic oligonucleotide

<400> SEQUENCE: 5
aaaggatcca agcttgaatt cctcgaga                                       28
```

```
<210> SEQ ID NO 6
<211> LENGTH: 28
<212> TYPE: DNA
<213> ORGANISM: Artificial
<220> FEATURE:
<223> OTHER INFORMATION: Synthetic oligonucleotide

<400> SEQUENCE: 6
tttcctaggt tcgaacttaa ggagctct                                    28

<210> SEQ ID NO 7
<211> LENGTH: 54
<212> TYPE: DNA
<213> ORGANISM: Artificial
<220> FEATURE:
<223> OTHER INFORMATION: Synthetic oligonucleotide

<400> SEQUENCE: 7
aaaggatcca agcttgaatt cctcgtttag cgcgtcgacg atatcggtac caaa       54

<210> SEQ ID NO 8
<211> LENGTH: 54
<212> TYPE: DNA
<213> ORGANISM: Artificial
<220> FEATURE:
<223> OTHER INFORMATION: Synthetic oligonucleotide

<400> SEQUENCE: 8
tttcttaggt tcgaacttaa ggagcaaacc gcgcagctgc tatagccatg gttt       54

<210> SEQ ID NO 9
<211> LENGTH: 54
<212> TYPE: DNA
<213> ORGANISM: Artificial
<220> FEATURE:
<223> OTHER INFORMATION: Synthetic oligonucleotide

<400> SEQUENCE: 9
aaaggatcca agcttgaatt cctcgtttag cgcgtcgacg atatcggtac caaa       54

<210> SEQ ID NO 10
<211> LENGTH: 54
<212> TYPE: DNA
<213> ORGANISM: Artificial
<220> FEATURE:
<223> OTHER INFORMATION: Synthetic oligonucleotide

<400> SEQUENCE: 10
tttcttaggt tcgaacttaa ggagcaaacc gcgcagctgc tatagccatg gttt       54

<210> SEQ ID NO 11
<211> LENGTH: 36
<212> TYPE: DNA
<213> ORGANISM: Artificial
<220> FEATURE:
<223> OTHER INFORMATION: Synthetic oligonucleotide

<400> SEQUENCE: 11
aaaggatcca agcttgaatt cctcgtttag cgcgtc                           36

<210> SEQ ID NO 12
<211> LENGTH: 36
<212> TYPE: DNA
<213> ORGANISM: Artificial
<220> FEATURE:
<223> OTHER INFORMATION: Synthetic oligonucleotide
```

```
<400> SEQUENCE: 12
tttcttaggt tcgaacttaa ggagcaaacc gcgcag                       36

<210> SEQ ID NO 13
<211> LENGTH: 40
<212> TYPE: DNA
<213> ORGANISM: Artificial
<220> FEATURE:
<223> OTHER INFORMATION: Synthetic oligonucleotide

<400> SEQUENCE: 13
aaaggatcca agcttgaatt cctcgtttag cgcgtcgacg                   40

<210> SEQ ID NO 14
<211> LENGTH: 40
<212> TYPE: DNA
<213> ORGANISM: Artificial
<220> FEATURE:
<223> OTHER INFORMATION: Synthetic oligonucleotide

<400> SEQUENCE: 14
tttcttaggt tcgaacttaa ggagcaaacc gcgcagctgc                   40

<210> SEQ ID NO 15
<211> LENGTH: 55
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (26)..(26)
<223> OTHER INFORMATION: n is a, c, g, or t

<400> SEQUENCE: 15
aaaggatcca agcttgaatt cctcgnagag atctgtcgac gatatcggta ccaaa  55

<210> SEQ ID NO 16
<211> LENGTH: 54
<212> TYPE: DNA
<213> ORGANISM: Artificial
<220> FEATURE:
<223> OTHER INFORMATION: Synthetic oligonucleotide

<400> SEQUENCE: 16
aaaggatcca agcttgaatt cctcgagaga tctgtcgacg atctcggtac caaa   54

<210> SEQ ID NO 17
<211> LENGTH: 54
<212> TYPE: DNA
<213> ORGANISM: Artificial
<220> FEATURE:
<223> OTHER INFORMATION: Synthetic oligonucleotide

<400> SEQUENCE: 17
tttcctaggt tcgaacttaa ggagctctct agacagctgc tatagccatg gttt   54
```

NANOPLASMONIC MOLECULAR RULER FOR NUCLEASE ACTIVITY AND DNA FOOTPRINTING

CROSS-REFERENCE TO RELATED APPLICATIONS

This application is a 371 National Stage filing of PCT/US07/20026, filed on Sep. 14, 2007, which claims benefit of and priority to U.S. Ser. No. 60/844,991, filed on Sep. 14, 2006, which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made during work supported by DARPA, NIH grant R21CA95393, and U.S. Department of Energy under Contract No. DE-AC02-05CH11231. The government of the United States of America has certain rights in this invention

FIELD OF THE INVENTION

The present invention relates to nucleic acid detection and footprinting using surface plasmon resonance.

BACKGROUND OF THE INVENTION

Nucleic acid-targeting proteins and enzymes are essential to various aspects of genetic information processing, such as replication, transcription, splicing, translation, recombination, DNA/RNA degradation, gene amplification/deletion/rearrangement, DNA repair, transposition, retroviral integration, and gene inactivation/silencing. The detection of size changes in nucleic acids is the key to diverse research areas such as nucleic acid-protein interaction mapping, nuclease inhibitor drug screening, and development of oligonucleotide-based therapeutics. The detection schemes usually require the synthesis of multiple special oligonucleotide substrates, and the labeling of the oligonucleotide(s) with fluorescent, electrochemical or radioactive probes (see, e.g., Behrens et al. (2004) *Syst. Appl. Microbiol.*, 27: 565-572; Smith and Anslyn (1994) *Anal. Biochem.*, 220: 53-57; Hillier et al. (2004) *Bioelectrochemistry* 63: 307-310), especially for nuclease-based methods. There remains the challenge of detection within small volumes and in real time, a problem made more pronounced with the advent of microarray and microanalytical devices, and the accompanying unprecedented reduction in assay volumes down to the nanoliter or even picoliter range.

As one of the promising technology platforms for measuring small changes, surface plasmon resonance (SPR) spectroscopy is an ultrasensitive optical method that measures the refractive index or dielectric constant of liquids or media in contact with the surface of metallic thin films. Conventional bulk-scale surface plasmon resonance sensors have been demonstrated to measure properties such as: the thickness of insulators, the refractive index of thin dielectrics, the detection of small molecules, analyte concentration, protein-protein/antibody-antigen interaction and dissociation kinetics, DNA hybridization, and mixture proportions.

SUMMARY OF THE INVENTION

This invention pertains to the development of a platform that allows for plasmon resonance sensing on a single nanoparticle at high speed for the detection of nucleic acid length changes. The system provides a rapid, easy and flexible approach for numerous methods to characterize nucleic acids and/or nucleic acid/protein (or other molecule) interactions in infinitesimal volumes (<fL).

According, in certain embodiments a nanoplasmon resonance ruler for calibrating nucleic acid length changes in a plasmon resonance system is provided. The ruler typically comprises a nanoparticle having a nucleic acid (e.g., single- or double-stranded DNA, RNA, DNA/RNA chimera, etc.) attached thereto to form a nanoparticle-nucleic acid conjugate, where the nucleic acid comprises at least two restriction sites positioned such that the conjugates cleaved at each of the restriction sites, provide plasmon resonance signatures that are distinguishable from the plasmon resonance signatures produced by the nucleic acid conjugates cleaved at the other restriction sites and/or the intact conjugate. In certain embodiments the nucleic acid is a double-stranded nucleic acid comprising a first strand attached to the nanoparticle and a second strand hybridized to the first strand, but not otherwise attached to the nanoparticle. In certain embodiments the nucleic acid comprises at least three, preferably at least four, more preferably at least five, six, or seven different restriction sites. In certain embodiments the nucleic acid further comprises at least one protein binding site, in certain embodiments, at least two, three, or at least four protein binding sites. In certain embodiments the nucleic acid ranges in length from 3 nucleotides (bp) to about 500 nucleotides (or bp), preferably from about 5 nucleotides (or bp) to about 200 nucleotides (or bp), more preferably from about 10, 20, 30, or 40 nucleotides (or bp) to about 60, 70, 80, or 100 nucleotides (bp). In various embodiments the nanoparticle is selected from the group consisting of a nanosphere, a nanocrescent, a nanowire, a nanohorn, a nanotube, a nanopyramid, a nanorod, a nanotetrepod, a single- or multi-layered nanodisk, and a nanohorn. In certain embodiments the nanoparticle comprises a metal or semiconductor material. In certain embodiments the nanoparticle comprises a material selected from the group consisting of a noble metal, a noble metal alloy, a noble metal composite. In certain embodiments the nanoparticle comprises a material selected from the group consisting of gold, gold alloy, silver, silver alloy, copper, copper alloy, platinum, platinum alloy, CdSe semiconductor, CdS semiconductor, CdSe coated with ZnS, magnetic colloidal materials, ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. In certain embodiments the nanoparticle comprises gold and/or silver. In certain embodiments the nanoparticle size ranges from about 5 nm to about 300, 200, or 150 nm, preferably from about 5 nm or 10 nm to about 30, 40, 50, 80, or 100 nm. In certain embodiments the nanoparticle surface is functionalized for attachment of the nucleic acid. In certain embodiments the nanoparticle surface is functionalized with a phosphine layer and/or using amino-silane molecules. In certain embodiments the conjugate comprises from about 10 to about 10,000 nucleic acid molecules per nanoparticle, preferably from about 50 to about 500, or 1,000 molecules per nanoparticle, more preferably from about 80 to about 150 molecules per nanoparticle, most preferably about 100 nucleic acid molecules per nanoparticle. In certain embodiments the nucleic acid is about 50-60 bp in length having a reactive group on one end to tether the nucleic acid to the nanoparticle. In certain embodiments the nucleic acid comprises a recognition site selected from the group consisting of a transcription factor binding site, a protein binding site, and an enzyme binding site. In certain embodiments the conjugate is immobilized (e.g., chemically immobilized, electrostatically immobilized, adsorbed, magnetically immobilized, etc.) on a substrate appropriate for surface plasmon resonance. In certain embodiments the conjugate is electrostatically immobilized on a glass, quartz, or ceramic surface.

Also provide is a substrate for identifying binding sites of molecules that bind to nucleic acids, and/or for detecting and/or quantifying such molecules, e.g., in a sample. The substrate typically comprises a substrate appropriate for surface plasmon resonance measurements bearing a collection of nanoplasmon resonance rulers attached thereto, each ruler comprising a nanoparticle having a nucleic acid attached thereto to form a nanoparticle-nucleic acid conjugate, whereby changes in the size of the nucleic acid are detectable through changes in the plasmon resonance signature of the conjugate, and where a plurality of members of the collection comprise different nanoconjugate species and the members are addressed. In certain embodiments the conjugates are spatially addressed. In certain embodiments the substrate bears at least three, preferably at least 5 or at least 10 different nanoconjugate species. In certain embodiments the nucleic acids are selected from the group consisting of a single-stranded DNA, a double-stranded DNA, a single-stranded RNA, and a double-stranded RNA. In certain embodiments the nucleic acids are double-stranded comprising a first strand attached to the nanoparticles and a second strand hybridized to the first strand, but not otherwise attached to the nanoparticles. In certain embodiments the nucleic acids comprise one or more binding site(s) for said molecule(s), (e.g., a protein binding site) and/or at least one restriction site. In certain embodiments the nucleic acids comprise a one or more protein binding sites and a plurality of restriction sites. In certain embodiments the nucleic acid(s) range in length from 3 nucleotides (bp) to about 500 nucleotides (or bp), preferably from about 5 nucleotides (or bp) to about 200 nucleotides (or bp), more preferably from about 10, 20, 30, or 40 nucleotides (or bp) to about 60, 70, 80, or 100 nucleotides (bp). In various embodiments the nanoparticle(s) are selected from the group consisting of a nanosphere, a nanocrescent, a nanowire, a nanohorn, a nanotube, a nanopyramid, a nanorod, a nanotetrepod, a single- or multi-layered nanodisk, and a nanohorn. In certain embodiments the nanoparticle(s) comprise a metal or semiconductor material. In certain embodiments the nanoparticle(s) comprise a material selected from the group consisting of a noble metal, a noble metal alloy, a noble metal composite. In certain embodiments the nanoparticle(s) comprise a material selected from the group consisting of gold, gold alloy, silver, silver alloy, copper, copper alloy, platinum, platinum alloy, CdSe semiconductor, CdS semiconductor, CdSe coated with ZnS, magnetic colloidal materials, ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. In certain embodiments the nanoparticles comprise gold and/or silver. In certain embodiments the nanoparticle size ranges from about 5 nm to about 300, 200, or 150 nm, preferably from about 5 nm or 10 nm to about 30, 40, 50, 80, or 100 nm. In certain embodiments the nanoparticle surface is functionalized for attachment of the nucleic acid. In certain embodiments the nanoparticle surface is functionalized with a phosphine layer and/or using amino-silane molecules. In certain embodiments the nanoconjugate(s) comprise from about 10 to about 10,000 nucleic acid molecules per nanoparticle, preferably from about 50 to about 500, or 1,000 molecules per nanoparticle, more preferably from about 80 to about 150 molecules per nanoparticle, most preferably about 100 nucleic acid molecules per nanoparticle. In certain embodiments the nucleic acid is about 50-60 bp in length having a reactive group on one end to tether the nucleic acid to the nanoparticle. In certain embodiments the nucleic acid comprises a recognition site selected from the group consisting of a transcription factor binding site, a protein binding site, and an enzyme binding site. In certain embodiments the conjugate is immobilized (e.g., chemically immobilized, electrostatically immobilized, adsorbed, magnetically immobilized, etc.) on the substrate. In certain embodiments the conjugate is electrostatically immobilized on a glass, quartz, or ceramic surface.

Also provided is a nanoplasmon resonance ruler comprising a nanoparticle having a nucleic acid attached thereto to form a nanoparticle-nucleic acid conjugate, whereby changes in the size of nucleic acid are detectable through changes in the plasmon resonance signature of the conjugate. In certain embodiments the nucleic acid is selected from the group consisting of a single-stranded DNA, a double-stranded DNA, a single-stranded RNA, and a double-stranded RNA. In certain embodiments the nucleic acid is a double-stranded nucleic acid comprising a first strand attached to the nanoparticle and a second strand hybridized to the first strand, but not otherwise attached to the nanoparticle. In certain embodiments the nucleic acid comprises at least three, preferably at least four, more preferably at least five, six, or seven different restriction sites and/or at least one protein binding site, in certain embodiments, at least two, three, or at least four protein binding sites. In certain embodiments the nucleic acid ranges in length from 3 nucleotides (bp) to about 500 nucleotides (or bp), preferably from about 5 nucleotides (or bp) to about 200 nucleotides (or bp), more preferably from about 10, 20, 30, or 40 nucleotides (or bp) to about 60, 70, 80, or 100 nucleotides (bp). In various embodiments the nanoparticle is selected from the group consisting of a nanosphere, a nanocrescent, a nanowire, a nanohorn, a nanotube, a nanopyramid, a nanorod, a nanotetrepod, a single- or multi-layered nanodisk, and a nanohorn. In certain embodiments the nanoparticle comprises a metal or semiconductor material. In certain embodiments the nanoparticle comprises a material selected from the group consisting of a noble metal, a noble metal alloy, a noble metal composite. In certain embodiments the nanoparticle comprises a material selected from the group consisting of gold, gold alloy, silver, silver alloy, copper, copper alloy, platinum, platinum alloy, CdSe semiconductor, CdS semiconductor, CdSe coated with ZnS, magnetic colloidal materials, ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. In certain embodiments the nanoparticle comprises gold and/or silver. In certain embodiments the nanoparticle size ranges from about 5 nm to about 300, 200, or 150 nm, preferably from about 5 nm or 10 nm to about 30, 40, 50, 80, or 100 nm. In certain embodiments the nanoparticle surface is functionalized for attachment of the nucleic acid. In certain embodiments the nanoparticle surface is functionalized with a phosphine layer and/or using amino-silane molecules. In certain embodiments the conjugate comprises from about 10 to about 10,000 nucleic acid molecules per nanoparticle, preferably from about 50 to about 500, or 1,000 molecules per nanoparticle, more preferably from about 80 to about 150 molecules per nanoparticle, most preferably about 100 nucleic acid molecules per nanoparticle. In certain embodiments the nucleic acid is about 50-60 bp in length having a reactive group on one end to tether the nucleic acid to the nanoparticle. In certain embodiments the nucleic acid is about 50-60 bp in length having a reactive group on one end to tether the nucleic acid to the nanoparticle. In certain embodiments the nucleic acid is dsDNA of SEQ ID NO: 11, where X in SEQ ID NO: 11 is any inserted DNA sequence or feature and ranges in length from about 3 to about 50 nucleotides. In certain embodiments X is selected from the group consisting of: transcription factor binding sites, mismatch sequences, single nucleotide polymorphisms, epigenetically changed sequence, protein binding site, and an enzyme binding site.

In certain embodiments the nucleic acid comprises a recognition site selected from the group consisting of a transcription factor binding site, a protein binding site, and an enzyme binding site. In certain embodiments the conjugate is immobilized (e.g., chemically immobilized, electrostatically immobilized, adsorbed, magnetically immobilized, etc.) on a substrate appropriate for surface plasmon resonance. In certain embodiments the nanoconjugate is electrostatically immobilized on a glass, quartz, or ceramic surface.

In certain embodiments methods of identifying the presence of and/or determining the location of a binding site of a molecule (or molecules) that binds to a nucleic acid are provided. The methods typically involve providing a conjugate comprising a nanoparticle attached to a nucleic acid comprising the binding site for the molecule(s), e.g., as described herein; contacting the conjugate ruler with a composition expected to contain the molecule(s) under conditions where the molecule binds to the nucleic acid to form a bound conjugate; digesting the nucleic acid with a non-specific exonuclease (or a specific exonuclease that would cleave at the site(s) bound by the molecule(s), but are blocked from such activity by the molecule(s) when bound) and detecting the change in nanoplasmon resonance resulting from the digestion, where the change in nanoplasmon resonance provides an indicator of the presence of the molecule and the location of the binding site of the molecule to the nucleic acid. In certain embodiments the molecule is a protein a transcription factor, or an enzyme.

In various embodiments methods of identifying the presence of and/or characterizing the binding site of a molecule are provided where the methods involve providing a collection of nanoplasmon resonance rulers (e.g., as described herein) where each ruler comprises a nanoparticle having a nucleic acid attached thereto to form a nanoparticle-nucleic acid conjugate (nanoconjugate), whereby changes in the size the nucleic acid are detectable through changes in the plasmon resonance signature of the conjugate, and where a plurality of members of the collection comprise different nucleic acids and the members are addressed; contacting the collection with the molecule under conditions where the molecule binds to one or more of the nucleic acids comprising the conjugate members of the collection to form a bound conjugate; digesting nucleic acids with a non-specific exonuclease (or a specific exonuclease that would cleave at the site(s) bound by the molecule(s), but are blocked from such activity by the molecule(s) when bound); and detecting the change in nanoplasmon resonance resulting from the digestion, where the change in nanoplasmon resonance provides an indicator of the nanoconjugates in the collection bound by the molecule, and the location of the binding site of the molecule on the nucleic acid(s). In various embodiments the conjugates are attached to a substrate compatible with plasmon resonance detection to form a substrate as described above. In certain embodiments the molecule is a protein, a transcription factor, or an enzyme.

Methods are also provided for detecting a mismatch in a nucleic acid hybridization. The methods typically involve providing a conjugate comprising a nanoparticle attached to a single-stranded nucleic acid probe (e.g., as described herein); contacting the nucleic acid probe with test nucleic acid under conditions where the test nucleic acid can hybridize to the probe nucleic acid despite the presence of a mismatch forming a double stranded nucleic acid; contacting the nucleic acid probe with a molecule that binds to the mismatch; and digesting the double-stranded nucleic acid with a non-specific exonuclease (or with a nuclease otherwise specific to the mismatch domain blocked by the mismatch binding protein) and detecting the change in nanoplasmon resonance resulting from the digestion, where the change in nanoplasmon resonance provides an indicator of the presence and location of the mismatch. In certain embodiments the molecule that binds the mismatch is selected from the group consisting of a protein that binds a single base mismatch, a protein that binds a bubble, a protein that binds a loop, a protein that binds a nick, a protein that binds a ssDNA-dsDNA transition, a protein that binds a flap, and a protein that binds a Y-fork. In certain embodiments the mismatch is the result of a polymorphism or a mutation. In certain embodiments the mismatch as a single base mismatch corresponding to an SNP. In certain embodiments the mismatch is the result of an insertion and/or a deletion as compared to the wildtype sequence. In certain embodiments the mismatch indicates a the species or strain of the organism from which the test nucleic acid is derived. In certain embodiments the test nucleic acid comprises a genomic DNA, a cDNA, and/or an mRNA.

Methods are provided for detecting a mismatch in a nucleic acid hybridization, where the methods involve providing a conjugate comprising a nanoparticle attached to a single-stranded nucleic acid probe (e.g., as described herein); contacting the nucleic acid probe with test nucleic acid under conditions where the test nucleic acid can hybridize to the probe nucleic acid despite the presence of a mismatch and where the mismatch results in portion of the strands directed away from the nanoparticle remaining single stranded; digesting the terminal single-stranded nucleic acid(s) with a single-strand specific exonuclease and detecting the change in nanoplasmon resonance resulting from the digestion, where the change in nanoplasmon resonance provides an indicator of the presence and location of the mismatch. In certain embodiments the mismatch is a frameshift mutation.

In certain embodiments methods for detecting a target feature or quantifying a binding event using a nanoplasmon resonance ruler are provided where the methods involve providing a Au-DNA nanoparticle conjugate comprised of a nanoparticle having a ssDNA oligonucleotide tethered thereto, where the oligonucleotide contains a restriction site; hybridizing a complementary oligonucleotide to the ssDNA oligonucleotide, where the complementary oligonucleotide contains a target feature or sequence to be probed is inserted at the restriction site; allowing a protein to bind to the target feature or sequence; performing DNA digestions using an exonuclease on the nanoconjugate; and observing time-lapse scattering spectra using surface plasmon resonance, where the plasmon resonance wavelength of the Au-DNA nanoparticle conjugate is measured as a function of time in the exonuclease reactions, whereby the size of the nanoconjugate and the binding event is detectable through the time-resolved measurement of the nanoplasmon resonance spectra.

DEFINITIONS

The terms "nucleic acid" or "oligonucleotide" refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977)

Eur. J. Biochem. 81: 579; Letsinger et al. (1986) Nucl. Acids Res. 14: 3487; Sawai et al. (1984) Chem. Lett. 805, Letsinger et al. (1988) J. Am. Chem. Soc. 110: 4470; and Pauwels et al. (1986) Chemica Scripta 26: 141 9), phosphorothioate (Mag et al. (1991) Nucleic Acids Res. 19:1437; and U.S. Pat. No. 5,644,048), phosphorodithioate (Briu et al. (1989) J. Am. Chem. Soc. 111: 2321, O-methylphophoroamidite linkages (see Eckstein, Oligonucleotides and Analogues: A Practical Approach, Oxford University Press), and peptide nucleic acid backbones and linkages (see Egholm (1992) J. Am. Chem. Soc. 114:1895; Meier et al. (1992) Chem. Int. Ed. Engl. 31: 1008; Nielsen (1993) Nature, 365: 566; Carlsson et al. (1996) Nature 380: 207). Other analog nucleic acids include those with positive backbones (Denpcy et al. (1995) Proc. Natl. Acad. Sci. USA 92: 6097; non-ionic backbones (U.S. Pat. Nos. 5,386,023, 5,637,684, 5,602,240, 5,216,141 and 4,469, 863; Angew. (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994), Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), Chem. Soc. Rev. pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments. Nucleic acids include single- or double-stranded nucleic acid, including, but not limited to single- or double-stranded DNA or RNA or DNA/RNA hybrids (chimeras). In various embodiments the nucleic acids range in length from about 5 to about 500 nucleotides (or base pairs for double stranded molecules), preferably from 5 to about 400, 300, or 200 nucleotides (or base pairs), more preferably from about 10, 5, 20, 25, 30, or 40 nucleotides (or base pairs) to about 150, 100, 80, or 60 nucleotides (or base pairs).

The term "nanoparticle" refers to a particle having a characteristic dimension of less than about 500 nm, preferably less than about 400 nm, more preferably less than about 300 nm, still more preferably less than about 200 or 100 nm, and most preferably less than about 80, 50, 40, or 30 nm. In certain embodiments the nanoparticle has a characteristic dimension (e.g., diameter) of about 20 nm.

The "size" of a nanoparticle refers to the size of the nanoparticle as determined by "characteristic length", e.g., a diameter for a sphere, or wire, the width for a rod, a length of a minor axis for an ellipsoid, the length of the shorter principle axis in general, and the like. In a population of nanoparticles, the size refers to the average size of the "characteristic length".

A "nanoplasmonic ruler" or nanoconjugate" as used herein refers to a structure comprising one or more nanoparticle(s) attached to a nucleic acid (single- or double-stranded).

A "collection of nanoconjugates" refers to a set of multiple species nanoconjugates distinguished by the nature of the attached nucleic acid. In various embodiments collections comprise at least 2, preferably at least 5 or 10, more preferably at least 20, 50, or 100, and most preferably at least 200, 500, 1,000, or 10,000 different nanoconjugates.

Nanoconjugates are said to be "different species" when they comprise a different nanoparticles or different nucleic acids (i.e., the nucleic acids differ in backbone, and/or sequence, and/or base modification).

When nanoconjugates are said to be "addressed", e.g., in a collection of nanoconjugates it indicates that different species of nanoparticles can be distinguished from each other (e.g., each species can be uniquely identified). In various embodiments the nanoconjugates can be spatially addressed by localizing different species at different locations on a substrate thereby forming a nanoconjugate "array". In certain embodiments the nanoconjugates can be addressed by providing a signature on the nanoconjugate unique to or identifiable as associated with each species. In various embodiments the signature can be provided by an attached label. In various embodiments the signature can be provided by a portion of the sequence of the nucleic acid comprising the nanoconjugate (e.g., permitting hybridization of, e.g., a labeled complementary decoding probe). In various embodiments the signature can be provided by the selection of material or materials comprising the nanoparticle(s) comprising the nanoconjugate.

A "DNA structure binding protein" refers to a protein that binds to a DNA structure generally independent of the sequence composition of that structure. DNA structure binding proteins include, but are not limited to proteins that bind to structures such as hairpins, loops, bubbles, nicks, ssDNA-dsDNA transition, ssRNA-dsRNAA transition, RNA-DNA transition, a flap, a Y-fork, and the like.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. Stringent hybridization and stringent hybridization wash conditions in the context of nucleic acid hybridization are sequence dependent, and are different under different environmental parameters. An extensive guide to the hybridization of nucleic acids is found in, e.g., Tijssen (1993) Laboratory Techniques in Biochemistry and Molecular Biology—Hybridization with Nucleic Acid Probes part I, chapt 2, Overview of principles of hybridization and the strategy of nucleic acid probe assays, Elsevier, N.Y. (Tijssen). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) Molecular Cloning: A Laboratory Manual (2nd ed.) Vol. 1-3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

"Relaxed hybridization conditions" refer to hybridization conditions that permit hybridization despite the occurrence of certain mismatches. In various embodiments the mismatch can be a single base mismatch. In various embodiments the mismatch can be a mismatch comprising up to 2, 3, 4, 5, 10, 15, 20, 25, 30, 35, 40, 45, or 50, or more base pairs (bps).

BRIEF DESCRIPTION OF THE DRAWINGS

FIG. 1A: Synthesis process of the single Au-DNA nanoconjugate. The 20 nm Au nanoparticle modified with a phosphine monolayer was enclosed by a layer of synthesized 54-bp dsDNA. A thiol group and FITC fluorophore were synthesized at each end of the dsDNA respectively. Through the thiol-Au chemistry, the dsDNA was tethered onto 20 nm Au nanoparticles. The dsDNA can be digested by four endonuclease enzymes, KpnI, SalI, XhoI, and HinDIII, with different incision lengths. FIG. 1B shows the sequence of the dsDNA (SEQ ID NO:1 upper strand and SEQ ID NO:2 lower strand). The incision sites of the enzymes are denoted on the respect positions of the dsDNA. The dsDNA contains restriction sites for the endonucleases HinDIII, XhoI, SalI, and KpnI, with their central incision positions at 12, 24, 36, and 48 bps from the Au nanoparticle-tethered end, respectively. The fluorescent labeling (FITC) is only for further confirmation of nuclease reactions, and thus not necessary for plasmon resonance measurements. The digestion of the synthesized dsDNA with the endonucleases was confirmed by gel electrophoresis (see, e.g., FIG. 6).

FIG. 2A shows TEM images of nanoconjugates: Panel a: Au; Panel b: Au-DNA; Panel c: Au-DNA with DNA stained by uranyl acetate (UA), which further increased the diameter of the complex (uneven DNA density is due to fixation); Panel d, distances between the Au nanoparticles. The error bars represent the standard deviation in the measurement of 50 nanoparticles. FIG. 2B shows electrophoresis of nanoconjugates: Panel a: Au-DNA nanoconjugates (Au-ph is phosphine-coated Au nanoparticle); Panel b: Au-DNA nanoconjugates cleaved by four endonucleases, which led to the loss of 42, 30, 18 and 6 bps from the dsDNA, showing DNA size-dependent mobility. FIG. 2C shows dark-field scattering images: Panel a: a single nanoparticle targeted and isolated from a field of Au-DNA nanoconjugates for spectroscopic examination; Panels b and c: true-color images of Au (panel b) (540 nm peak) and Au-DNA (panel c) (607 nm peak). FIG. 2D shows scattering spectra of Au and Au-DNA.

FIG. 3A: Plasmon resonance sensing with multiple nanoconjugates: Panels a-c show dark-field scattering images of the Au-DNA nanoconjugates cleaved by endonuclease XhoI (panel a, before cleavage; panel b, 1 hour reaction with more than 90% cleavage; panel c, 16 hours reaction with 100% cleavage. See also FIG. 8 for validated cleavage). Panel d shows plasmon resonance wavelengths of the single Au nanoconjugates in FIG. 3A, panels a-c. The error bars represent the standard deviation in the measurement of 20 nanoparticles. FIG. 3B, panels a-c, shows real-time plasmon resonance sensing of endonuclease reactions: Panel a: raw scattering spectra data of a single Au-DNA nanoconjugate in an endonuclease reaction, time-resolved; Panel b: plasmon resonance peak wavelength; Panel c: scattering peak intensity of the Au-DNA nanoconjugate in the 30-min reactions with 1:1 XhoI (3.5 nM, circles), 1:10 XhoI (350 pM, triangles), control buffer only (diamonds) and inhibitor/chelator EDTA (squares). The plasmon resonance wavelength data exhibit a first-order exponential decay (red and orange curves).

FIG. 4A shows typical scattering spectra. FIG. 4B shows plasmon resonance peak wavelengths of the Au-DNA nanoconjugates after cleavage reactions with four endonuclease enzymes, and as a function of the number of base pairs remaining attached to the Au nanoparticle after the cleavage. The red curve is a fit from a semi-empirical model using a Langevin-type dependence of the refractive index versus dsDNA length (see FIG. 9 and Table 1). The error bars represent the standard deviation in the measurement of 20 nanoparticles.

FIG. 5A shows a schematic diagram of footprinting by Bal31 and the stalled Bal31 hydrolysis by DNA-bound EcoRI(Q111) protein. The EcoRI(Q111) blocks nucleotide removal by Bal31 on a single Au-DNA nanoconjugate (full length upper strand (SEQ ID NO:3), full length lower strand (SEQ ID NO:4), digested upper strand (SEQ ID NO:5), digested lower strand (SEQ ID NO:6)). FIGS. 5B and 5C show time-lapse scattering spectra of the single Au-DNA nanoconjugates without EcoRI(Q111) (FIG. 5B) and with EcoRI(Q111) (FIG. 5C) during exonuclease Bal31 hydrolysis. FIG. 5D shows plasmon resonance wavelength of the Au-DNA nanoconjugate as a function of time in the exonuclease reactions, with wavelength shift shown on the right vertical axis and the base pair of the dsDNA removed on the left vertical axis. The error bars represent the standard deviation in the measurement of 10 nanoparticles.

FIGS. 15A-15D illustrate examples of DNA sequence design for various applications as described herein, e.g., for detection and identification of (FIG. 15A) transcription factors (SEQ ID NO:7 upper strand, SEQ ID NO:8 lower strand), (FIG. 15B) SNPs (SEQ ID NO:9 upper strand, SEQ ID NO:10, lower strand), (FIG. 15D) mismatch DNA (SEQ ID NO:11 upper strand, SEQ ID NO:12, lower strand), (FIG. 15E) transcriptional factor E2F1 bound to CYCD1 gene promoter binding site (SEQ ID NO:13 upper strand, SEQ ID NO:14, lower strand).

DETAILED DESCRIPTION

Figure 1A:
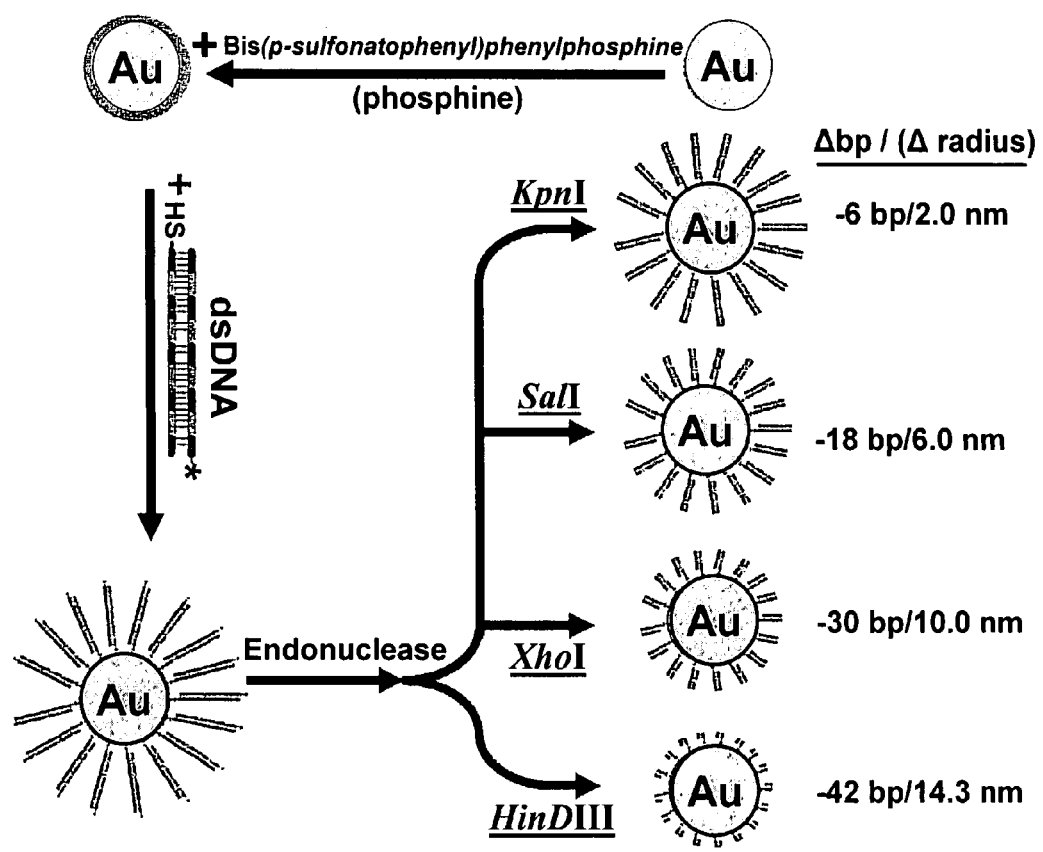
FIGS. 1A and 1B illustrate the design of a gold-DNA nanoplasmonic molecular ruler.

This invention provides novel compositions and methods for investigating/characterizing the interactions of nucleic acids and other molecules that bind to nucleic acids. In particular, in certain embodiments, this invention provides a nanoplasmonic molecular ruler, which can perform label-free and real-time monitoring of nucleic acid (e.g., DNA) length changes and perform nucleic acid footprinting. The ruler is created by tethering single- or double-stranded nucleic acids to single nanoparticles (e.g., gold nanoparticles) to form nucleic acid nanoconjugates. The scattering spectra of nanoconjugates shows red-shifted peak plasmon resonance wavelength dependent on nucleic acid length, which can be measured with sub-nanometer axial resolution, averaging in the case of DNA, ~1.24 nm peak wavelength shift per DNA base pair. The spectra of individual nanoconjugates in the presence of a nuclease shows a time-resolved dependence on the reaction dynamics, allowing quantitative, kinetic and real-time measurement of nuclease activity.

The ruler provides a quantitative calibration to establish a relationship between length change and shift in the Plasmon resonance peak. This calibration can be utilized to provide an accurate realtime measurement of nanoconjugate nucleic acid length and/or length change, e.g., in response to nuclease cleavage.

In certain embodiments using such calibration, the nanoplasmonic rulers can be used to detect and characterize (e.g., identify the binding domain of) the binding of the nanoconjugate nucleic acid by another molecule (e.g. a protein, transcription factor, enzyme, etc.). The system can similarly be used to detect and/or localize mismatches in nucleic acid hybridization reactions and thereby identify nucleic acid features including, but not limited to, polymorphisms, mutations, and the like.

This invention thus provides a very fast and convenient platform for mapping nucleic acid-protein interactions, for nuclease activity monitoring, and for other nucleic acid size-based methods. In various embodiments methods are provided for using the nanoplasmonic molecular ruler for detection of a specific sequence, base pair changes, mutations, size, structure, or feature of a sample DNA by surface plasmon resonance (SPR), e.g., as described herein.

I. Nanoplasmonic Rulers and Use thereof.

A) Detection and Quantification of Nucleic Acid Size and Size Change.

The nanoplasmonic rulers (nucleic acid nanoconjugates) of this invention provide a plasmon resonance signal (e.g., nanoplasmon resonance peak) signal that is highly sensitive to changes in nucleic acid length. Thus, in certain embodiments methods and compositions are provided for calibrating the relationship between signal and nucleic acid length change.

In certain embodiments this is accomplished by providing double-stranded nucleic acids attached to the nanoparticles, where the double-stranded nucleic acids. The double stranded nucleic acid(s) are designed to contain multiple endonuclease restriction sites so that, after performing DNA digestions on the nanoconjugate, using corresponding endonuclease(s) the size of the nanoconjugate is detectable through the time-resolved measurement of the nanoplasmon resonance signatures. Different endonuclease digestion sites can be distinguished from each other by the resulting plasmon resonance wavelength change, which corresponds to the different lengths of DNA remaining attached to the nanoparticle after digestion. In various embodiments, using double stranded DNA, this provides a resolution of ~1.24 nm wavelength shift per DNA by on average.

Figure 1B:
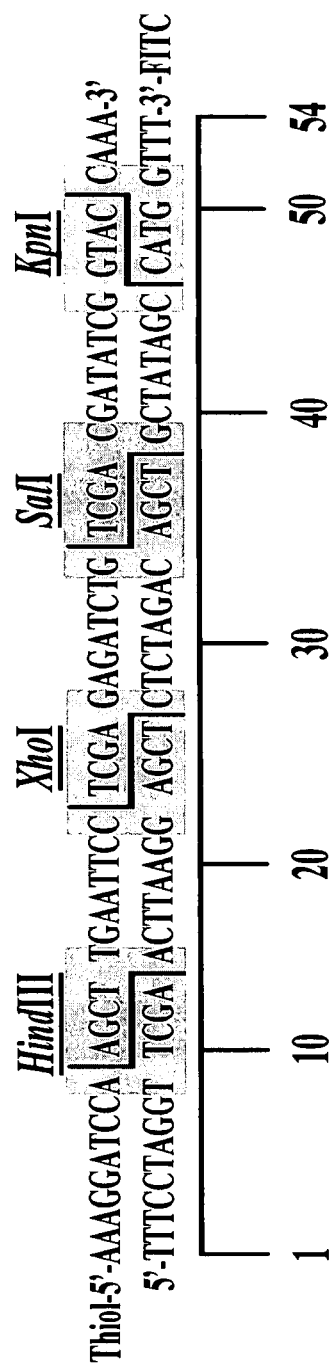

Referring now to FIGS. 1A and 1B by way of illustration, in certain embodiments, the incision sites for the enzymes are designed/selected so they are located at varying positions of the dsDNA to allow the generation of a standard curve. Thus, the restriction sites are typically located so as to produce different an distinguishable signals upon endonuclease digestion and sufficient restriction sites are provided to generate a standard curve of the desired resolution and/or accuracy. Methods for generation of a standard curve using the nanoplasmonic resonance ruler are described in the Examples.

For example, in one embodiment, where the oligonucleotide is 54-bp in length, the dsDNA contains restriction sites for the endonucleases HinDIII, XhoI, SalI, and KpnI, with their central incision positions at 12, 24, 36, and 48 bps from a gold nanoparticle-tethered end, respectively. Thus, when the oligonucleotide is digested by 4 endonuclease enzymes, such as KpnI, SalI, XhoI, and HinDIII, it results in a nano-conjugate with oligonucleotides having different incision lengths.

While, in certain embodiments, fluorescent labeling (FITC) can be added for further confirmation of nuclease reactions. It is not necessary for plasmon resonance measurements. The digestion of the synthesized dsDNA with the endonucleases can be confirmed by gel electrophoresis.

Any nucleic acid (e.g., DNA) restriction site and corresponding enzyme(s) are suitable for use in the present method provided the target restriction sequence is present in the nucleic acid comprising the nanoconjugate. Methods for performing the endonuclease digestion reactions are well know to those of skill in the art. Thus, for example, in the Examples, restriction digestion of DNA with restriction endonucleases HinDIII, KpnI, XhoI, and SalI is performed according to the manufacturer's instructions (New England Biolab), modifying the protocol only to remove the reducing reagent from the reaction buffer and the enzymes, in order to avoid detachment of the thiolated DNA from the gold nanoparticles.

While the calibration is illustrated in the example using double-stranded DNA, similar calibrations can be performed using double stranded RNA, DNA/RNA hybrids and the like.

Moreover, the methods are not limited to the use of restriction endonucleases. Any convenient method of digesting (hydrolyzing) the singe- or double-stranded nucleic acid to a particular (e.g., predetermined) length can be utilized.

Thus, for example, in certain embodiments, a single-stranded nucleic acid is provided attached to the nanoconjugate. The single strand is hybridized to complementary strands of different lengths thereby forming nanoconjugates comprising a double-stranded nucleic acid terminating in a single-stranded nucleic acids of different lengths. The nano-conjugates are digested with an exonuclease (e.g., Exonuclease I) specific for single stranded nucleic acids so the reaction terminates when it reaches the double stranded portion. The change in plasmon resonance signal can be determined and a calibration curve calculated. Conversely, the reaction can be done using exonucleases specific for double stranded nucleic acids.

Alternatively the single- or double-stranded nucleic acids can be hydrolyzed with any suitable reagent or enzyme, the change in plasmon resonance signature determined, and the resulting length of the nucleic acid subsequently determined (e.g., via mass spectroscopy, electrophoresis, sequencing, and the like).

These methods are intended to be illustrative and not limiting. Using the methods described herein, other methods of generating calibration standards and/or a calibration curve will be recognized by those of skill in the art.

B) Illustrative Applications.

Upon the generation of standard calibration curves using the nanoplasmon resonance ruler as described, the nanoplasmonic ruler then provides a nucleic acid footprinting platform with resolution comparable to conventional radioactive methods. The detection of the presence of a specific feature (i.e., sequence, mutation, structure or feature) in a nucleic acid sample or of a protein bound to the target sequence or feature, can then be performed using the nanoplasmon resonance ruler. Furthermore, using the nucleic acid-nanoparticle conjugate in array format provides a platform that permits simultaneous detection of multiple features in the sample.

Thus, in certain embodiments, the nucleic acid comprising the nanoconjugate contains a binding site for a protein. In various embodiments the oligonucleotide contains a specific sequence to be probed.

1) Detecting and/or Footprinting Binding Proteins.

In certain embodiments the nanoplasmon rulers of this invention can be used to detect and/or footprint DNA binding proteins. Such DNA binding proteins, include, but are not limited to transcription factors, nucleases, histones, and the like.

For example, by way of illustration, in one embodiment, footprinting of a cleavage-defective EcoRI(Q111) mutant on DNA is shown. Example 1 describes DNA footprinting of exonuclease stalled by the EcoRI(Q111) proteins. The cleavage-defective EcoRI(Q111) binds to GAATTC site on the DNA and blocks nucleotide removal by BAL31 on a single Au-DNA nanoconjugate. The dsDNA is digested completely by the BAL31 enzyme in the absence of the cleavage-defective EcoRI(Q111) mutant. However, after binding with EcoRI(Q111) mutant, the exonuclease digestion is stalled at the binding position resulting in the time-lapse scattering spectra of the single Au-DNA nanoconjugate with EcoRI(Q111) mutant during the exonuclease BAL31 digestion in FIG. 5C as compared to the time-lapse scattering spectra of the single Au-DNA nanoconjugate without EcoRI(Q111) mutant during the exonuclease BAL31 digestion in FIG. 5B.

The plasmon resonance wavelength of a single nanoconjugate in each of these two samples was monitored throughout the digestion reactions. Plasmon resonance wavelength of the Au-DNA nanoconjugate was measured as the function of time in the exonuclease reactions, with wavelength shift shown on right Y axis. Also shown on the left y axis is the digested base pair of the dsDNA as the function of time in the exonuclease reactions. The Bal31 maps the distal boundary of the DNA footprint to ~25 bp from the distal end of the DNA. Other exonucleases with dsDNA digestion activity can be used in place of BAL31.

While Example 1 illustrates the use of a simple dsDNA nanoparticles conjugate as proof of concept, there is no limitation to either the sequences, or structure of the nucleic acid substrates that can be conjugated. The nanoconjugate can, in various embodiments, include numerous different DNA structures, including, but not limited to stem-loops, nicks, ssDNA-dsDNA transition, flaps, Y-forks, dsRNA, etc. The ability to resolve a single nanoparticle quickly also makes it possible to perform high-throughput screening in a microarray format or in microfluidic devices.

2) Detecting and/or Footprinting Transcription Factors.

Figure 10A:
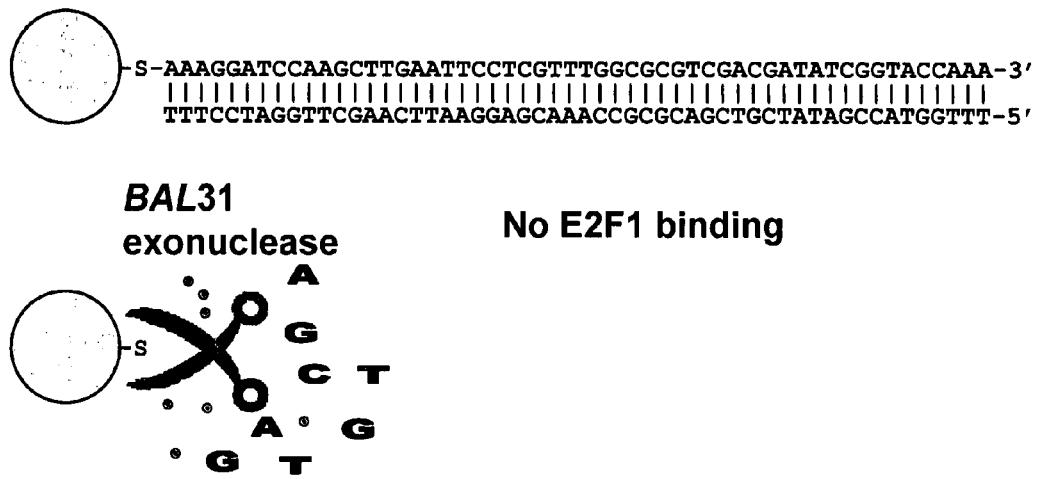
FIGS. 10A and 10B show a schematic diagram of footprinting on the nanoplasmonic ruler to detect binding a transcription factor (e.g., E2F1). Absent binding by E2F1 (or other binding protein) digestion of the nucleic acid by BAL31 exonuclease is substantially complete (FIG. 10A). Digestion of the molecular ruler nucleic acid by BAL31 exonuclease is stalled when the transcription factor is present providing a signal that indicates the presence and binding location of the transcription factor (FIG. 10B).
Figure 10B:
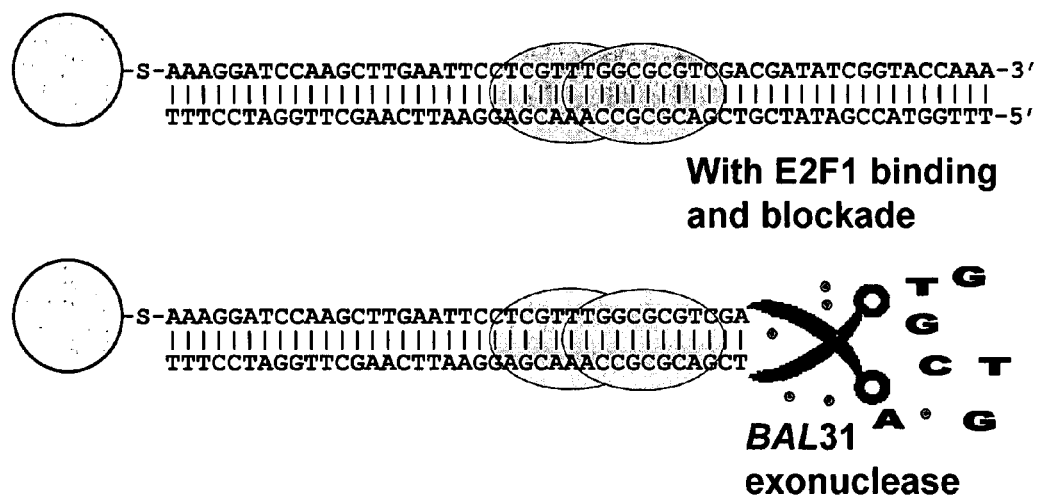

FIG. 10 shows the detection and footprinting of a transcription factor. Similar to the EcoRI(Q111) example, the transcription factor binds to the DNA at a transcription factor binding site. The bound transcription factor blocks digestion by the BAL31 exonuclease stalling the reaction at that point. In contrast, the dsDNA is completely digested by the BAL31 enzyme in the absence of the transcription factor. A time-lapse scattering spectra of the single DNA-nanoparticle nanoconjugate with the transcription factor bound during the exonuclease BAL31 digestion is compared to the time-lapse scattering spectra of the single DNA-nanoparticle nanoconjugate without the transcription factor bound. Thus, the nanoplasmonic ruler can be used to detect and quantify the activity of transcriptional factors with sequence specific binding on DNA.

Where the binding site of the transcription factor is unknown, a population (collection) of nanoplasmon rulers (nucleic acid nanoconjugates) having different nucleic acid sequence can be used. Those nanoconjugates having a binding site will stall digestion by BAL31, while those lacking the binding site will be fully digested. Thus the binding site can be detected and identified.

3) Detecting and/or Quantifying or DNA Base Modifications.

Figure 11A:
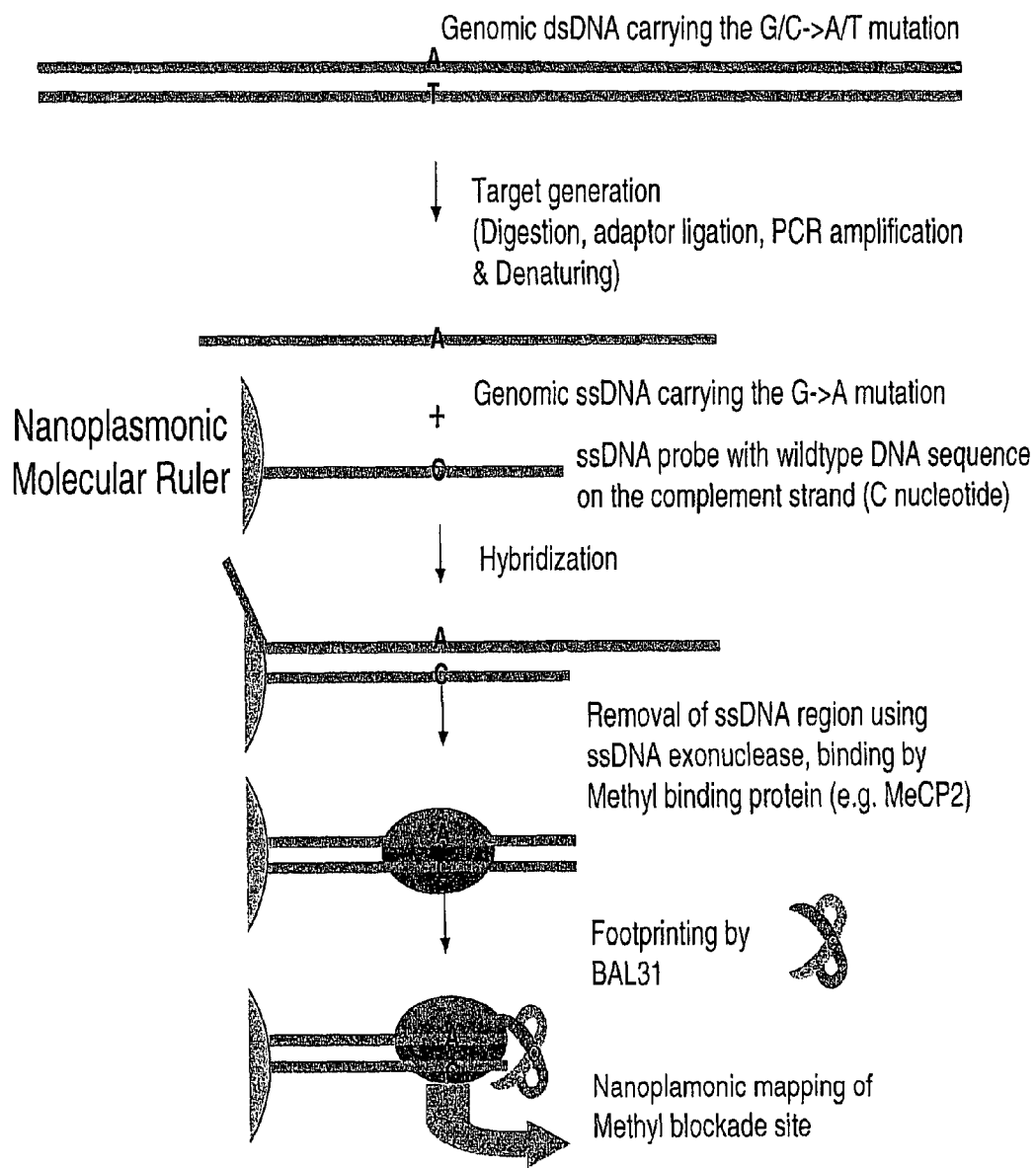
FIGS. 11A and 11B illustrate the detection of single nucleotide polymorphisms (SNPs) using methyl binding proteins such as MeCP2 (FIG. 11A) or mismatch binding proteins such as MutS (FIG. 11B). Digestion of the molecular ruler nucleic acid by an exonuclease (e.g., BAL31) is stalled when the methyl binding protein or mismatch binding protein is present providing a signal that indicates the presence and location of the SNP.
Figure 11B:
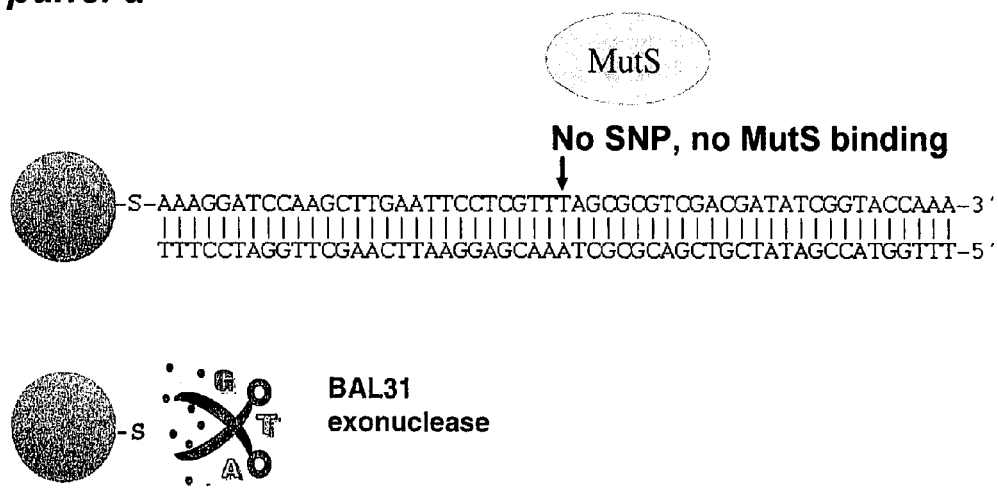
Figure 11B:
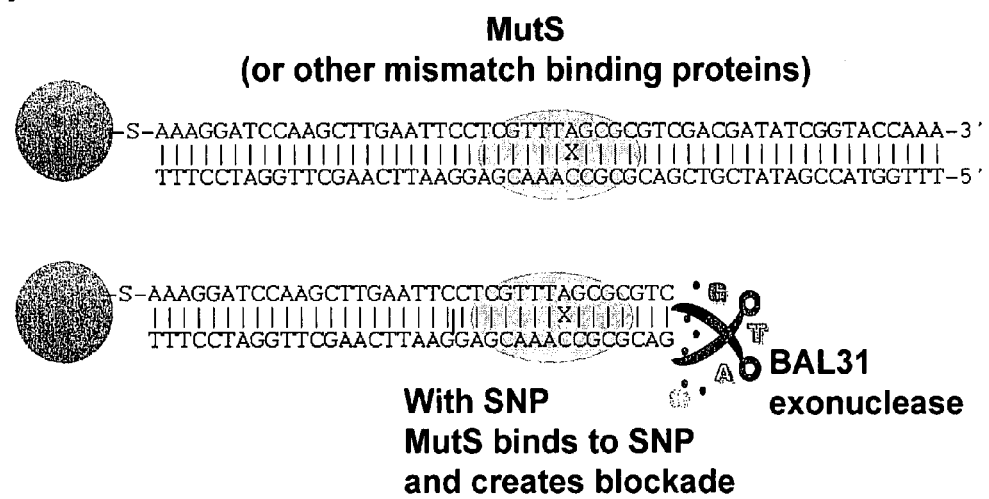

FIGS. 11A and 11B schematically illustrate footprinting using the present nanoplasmonic ruler to detect and quantify DNA base modifications and single nucleotide polymorphisms (SNPs) present in DNA, or mismatch sites in DNA when more than a single nucleotide is mutated. In one embodiment, as shown in FIG. 11A, a methyl binding protein, such as MeCP2, binds to methylated DNA nucleotide base on the DNA and blocks nucleotide removal by BAL31 e.g., on a single DNA-nanoparticle nanoconjugate, thereby stalling exonuclease digestion at the binding position. A time-lapse scattering spectra of the single DNA-nanoparticle nanoconjugate with the methyl binding protein bound during the exonuclease BAL31 digestion is compared to the time-lapse scattering spectra of the single DNA-nanoparticle nanoconjugate without the methyl binding protein bound to identify the presence and/or site of methylation thereby identifying a base modification (e.g., methylation).

4) Detecting and/or Identifying/Localizing Mismatches or SNPs.

In another embodiment, illustrated in FIG. 11B, a mismatch binding protein, such as MutS, binds to a mismatch site on the DNA (e.g., where complementarity is disrupted due to a single nucleotide polymorphism (SNP). The bound MutS nucleotide removal (digestion) by BAL31 on the DNA-nanoparticle nanoconjugate. In contrast, nanoconjugate lacking the mismatch is not bound by MutS and is fully digestion. Thus, the nanoplasmonic ruler can be used to detect and quantify single nucleotide polymorphisms with sequence specific binding on DNA.

In certain embodiments the nanoconjugates comprise nucleic acids that are complementary to wild type sequences. They are hybridized with a genomic DNA, mRNA, or cDNA generated from a sample. The hybridization conditions are sufficiently relaxed to permit single base mismataches. The hybridized nanoconjugates are contacted with MutS. If there is a mismatch, e.g., due to the presence of an SNP in the sample, the MutS will bind to the mismatch site(s). Digestion by, e.g., BAL31 will be stalled on these mismatch-containing nanoconjugates, thereby indicating the presence and location of the mismatch.

Figure 12:
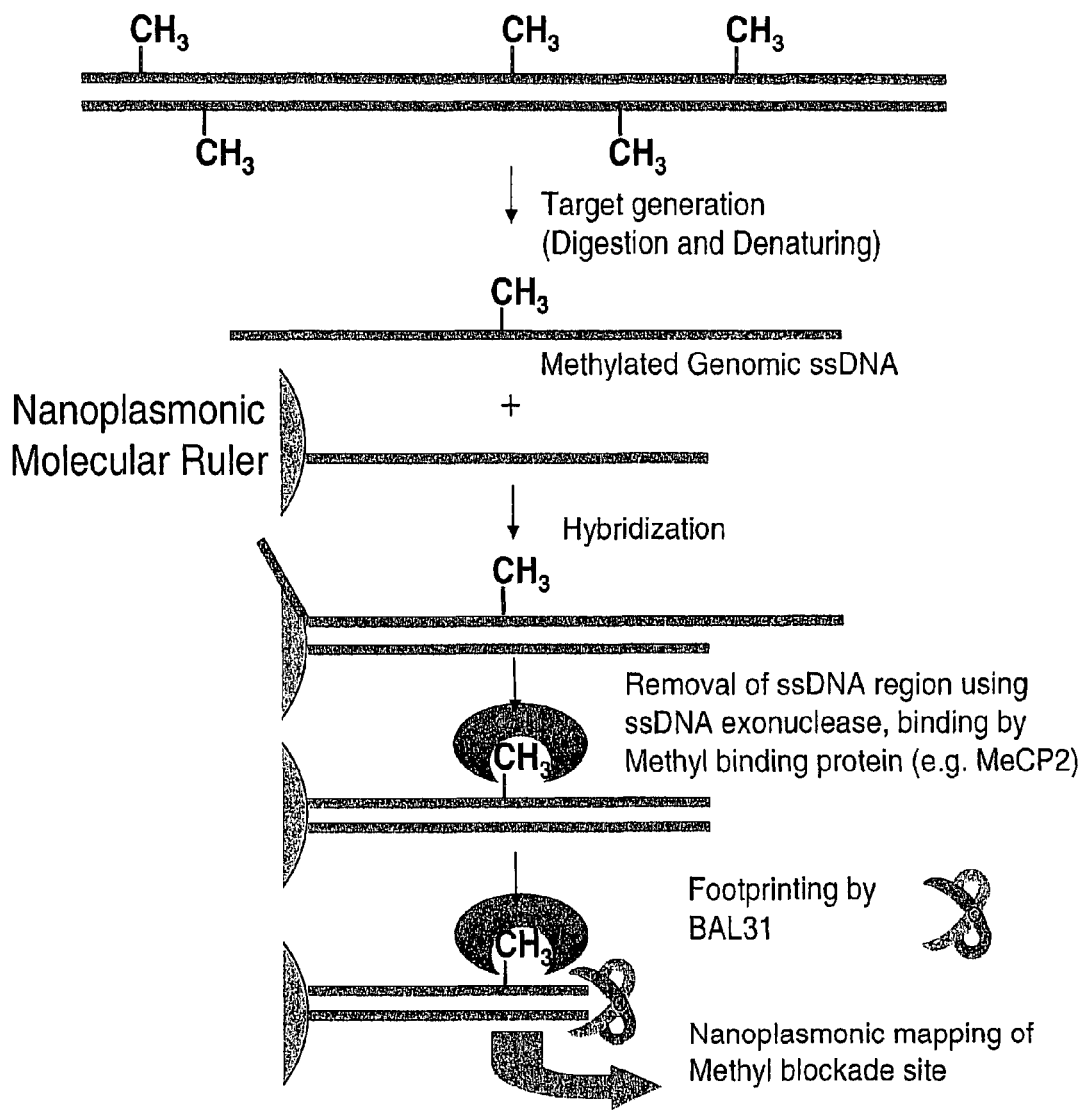
FIG. 12 illustrates the use of footprinting using the nanoplasmonic ruler to identify epigenetic changes on DNA.

In certain embodiments, it is contemplated that the methods described herein application can be used to detect SNPs and/or epigenetic methylated bases in, for example, a DNA sample from a patient as shown for example in FIGS. 11B and 12. It is also contemplated that multiple types of SNPs can be probed at one time by allowing, e.g., a patient's DNA to hybridize to a nanoconjugate collection or array, where oligonucleotides featuring the wild type sequence of many SNPs are tethered to nanoparticles. After hybridization, a mismatch binding protein (e.g. MutS, or other mismatch binding proteins) is added to identify and bind to any SNPs. After a ssDNA exonuclease is added to digest the DNA, mutations can be detected by plasmon resonance by observation of a peak at the SNP loci.

5) Footprinting Epigenic Changes in Disease and other States.

Referring to FIG. 12, a schematic diagram shows footprinting of epigenetic changes on genomic DNA using the nanoplasmonic ruler. In cancer and other diseases, many regulatory genes, such as p53 and BRCA1/BRCA2, are epigenetically changed. Such epigenetic changes that can be detected and quantified by the present nanoconjugates include but are not limited to, methylation, acetylation, ubiquitylation, and the like. In certain embodiments genomic single stranded DNA from a patient sample is provided and hybridized to the nanoplasmonic ruler. A specific binding protein is then provided and binds to the modified site on the DNA and blocks nucleotide removal by BAL31 on a single Au-DNA nanoconjugate. The dsDNA is digested completely by the BAL31 enzyme in the absence of the protein bound to the epigenetic change. However, after binding with the protein, the exonuclease digestion is stalled at the binding position. A time-lapse scattering spectra of the single DNA-nanoparticle nanoconjugate with the protein bound during the exonuclease BAL31 digestion is compared to the time-lapse scattering spectra of the single DNA-nanoparticle nanoconjugate without protein bound. Thus, the nanoplasmonic ruler can be used to detect and quantify epigenetic changes with sequence specific binding on DNA.

6) Detecting and/or Localizing Nucleic Acid Structures

Figure 13:
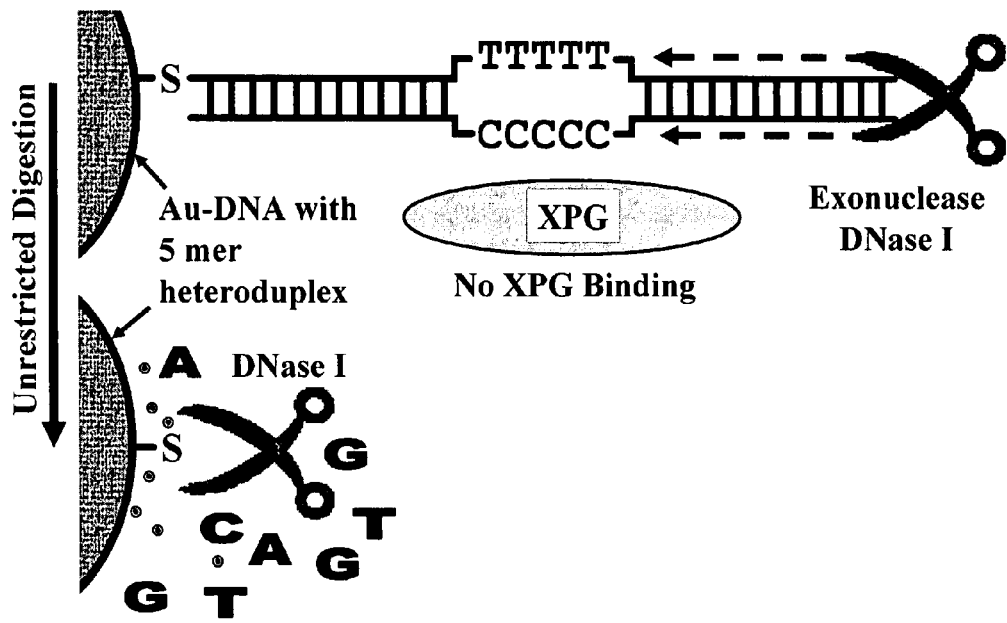
FIG. 13 illustrates footprinting using the nanoplasmonic ruler to detect and footprint the proteins that bind specifically to structures on a nucleic acid (e.g. a DNA bubble structure bound by XPG protein). In this example, XPG does not bind to a bubble of 5 base pairs, but it binds to 10-15 bps bubbles. Thus, as shown in panel A, XPG doesn't' bind to the ruler and the nucleic acid is completely digested. In panel B, a larger bubble is present. Digestion of the molecular ruler nucleic acid by an exonuclease (e.g., BAL31) is stalled when the structure binding protein (e.g., XPG) is present thereby providing a signal that indicates the presence and location of the structure.
Figure 13:
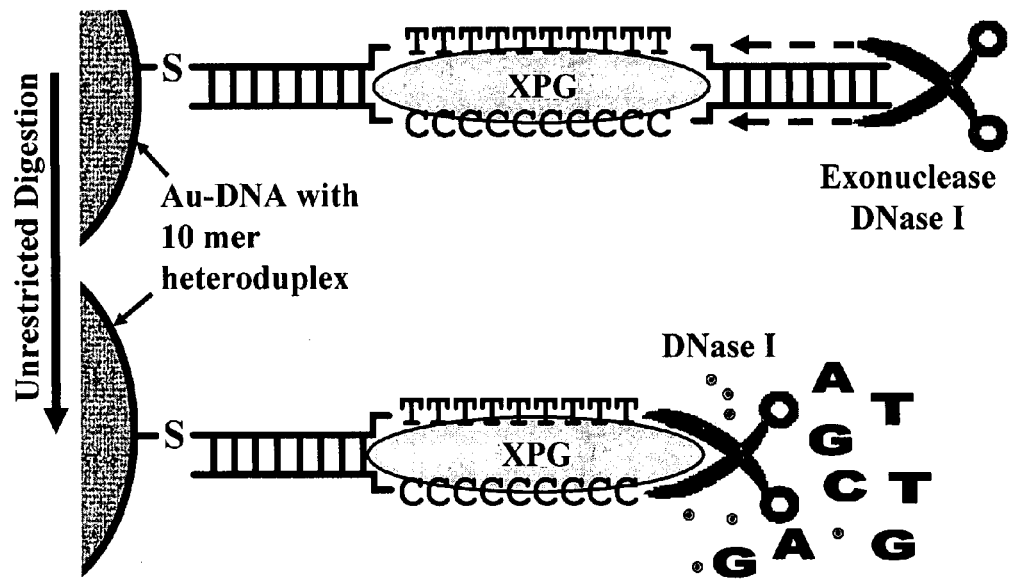

FIG. 13 shows a schematic diagram illustrating footprinting using the nanoplasmonic ruler(s) of this invention to detect and footprint proteins that bind specifically to structures (other than sequence specific binding) on DNA (e.g. DNA bubble structures bound by XPG protein). DNA structures that can be identified include but are not limited to, 5 bp bubbles, 10 bp bubble, stem loops, and overhangs. In one embodiment, as shown in FIG. 13, a DNA structure binding protein, such as XPG, binds to the identified structure on the DNA and blocks nucleotide removal by a nuclease such as BAL31 on a single DNA-nanoparticle nanoconjugate. The dsDNA is digested completely by the BAL31 enzyme in the absence of XPG. However, after binding with the structure binding protein, the exonuclease digestion is stalled at the binding position. A time-lapse scattering spectra of the single DNA-nanoparticle nanoconjugate with the DNA structure binding protein bound during the exonuclease BAL31 digestion is compared to the time-lapse scattering spectra of the single DNA-nanoparticle nanoconjugate without the structure binding protein bound.

Figure 14:
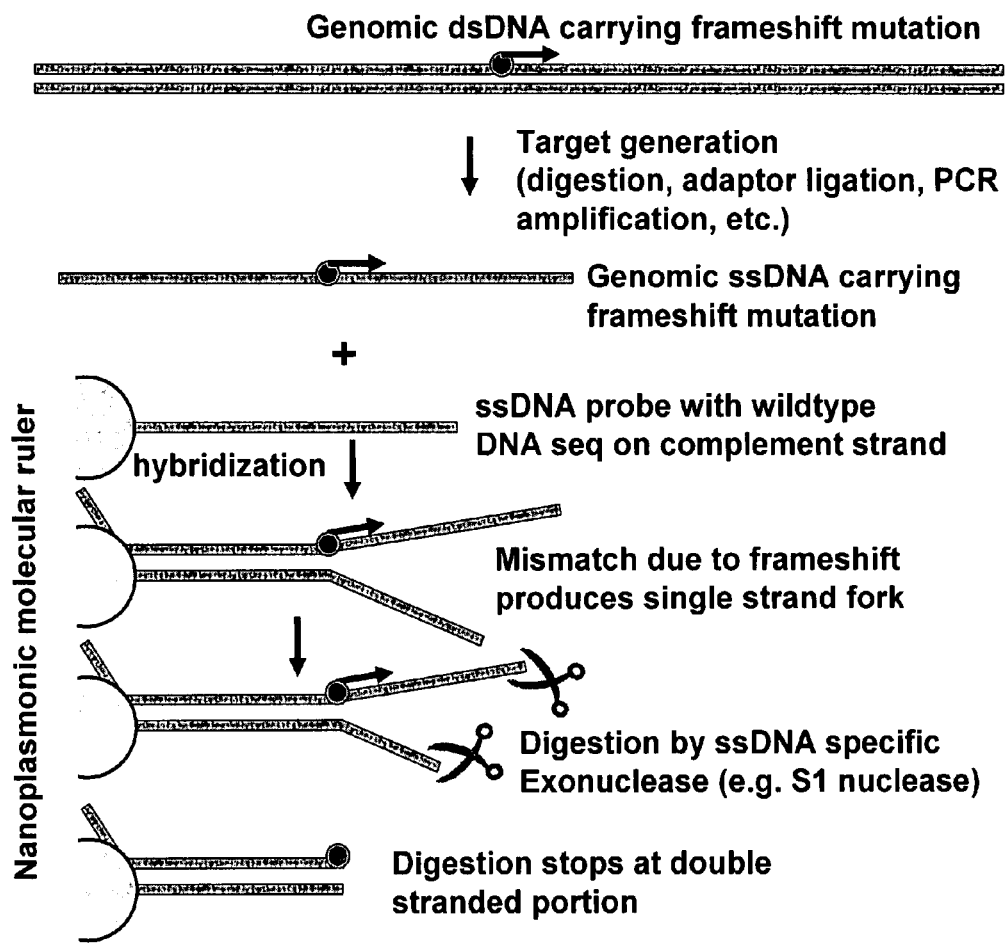
FIG. 14 illustrates detection of a mismatch mutation without the use of a binding protein. Genomic DNA, mRNA, or cDNA (e.g., RTcDNA) containing a frameshift mutation is hybridized to the nanoplasmonic ruler containing a wildtype nucleic acid probe. Because of the mismatch, the hybridization produces a Y (split) DNA terminating in two single strands. The single strands are digested using a single strand specific exonuclease which terminates digestion at the location of the frameshift. Where the target nucleic acid does not contain the frameshift, the entire probe will be hybridized resulting in no single strands and no digestion by the enzyme. Digestion of the single stranded portion of the hybridized nucleic acids (e.g., using S1 nuclease) provides a signal that indicates the presence and location of the mismatch.

7) Detecting and/or Localizing Nucleic Acid Structures without Using Binding Proteins In various embodiments, certain nucleic acid structures can be detected and/or localized without using a structure binding protein. This is illustrated for example, in FIG. 14, which shows the detection of frameshift mutation without the use of a binding protein. Genomic DNA, mRNA, or cDNA (e.g., RTcDNA) containing a frameshift mutation is hybridized to the nanoplasmonic ruler containing a wildtype nucleic acid probe. Because of the mismatch, the hybridization produces a Y (split) DNA terminating in two single strands. The single strands are digested using a single strand specific exonuclease which terminates digestion at the location of the frameshift. Where the target nucleic acid does not contain the frameshift, the entire probe will be hybridized resulting in no single strands and no digestion by the enzyme. Digestion of the single stranded portion of the hybridized nucleic acids (e.g., using S1 nuclease) provides a signal that indicates the presence and location of the mismatch.

While the foregoing examples are illustrates with reference to specific endonucleases, exonucleases (e.g., Bal31), single-strand specific exonucleases (e.g., S1), structure-specific binding proteins (e.g., XPG), mismatch-specific binding proteins' (e.g. MutS), and modification specific binding proteins (e.g., MeCP2) other species of such proteins are well know to those of skill in the art and can be used in the methods described herein.

FIGS. 15A-15D illustrate various nucleic acid sequences for incorporation in the nanoplasmon rulers of this invention.

8) Other Illustrative Applications.

There is also an abundance of potential nuclease targets in diverse areas of research and applications, such as HIV integrase (Caumont et al. (1999) *FEBS Lett* 455: 154-158; Rumbaugh et al. (1988) *J Biol Chem* 273: 28740-28745; Nair (2002) *Rev Med Virol* 12: 179-193) (HIV drugs), apoptosis-activated DNases (Counis and Torriglia (2000) *Biochem Cell Biol* 78: 405-414; Fan (2003) *Cell* 112(5): 659-672) (anti-apotic drugs), and microRNA/siRNA processing RNases (Moss (2001) *Curr Biol* 11: R772-775; Tijsterman and Plasterk (2004) *Cell* 117: 1-3) (siRNA stability) or WRN (Kamath-Loeb et al. (1998) *J Biol Chem* 273: 34145-34150; Shen et al. (1998) *J Biol Chem* 273: 34139-34144) and V(D)J-rejoining enzyme RAG recombinases (Roth (2003) *Nat Rev Immunol* 3: 656-666; Shockett and Schatz (1999) *Mol Cell Biol* 19: 4159-4166) (radiosensitizer drugs).

The nanoparticles conjugates can also be tracked in vivo, and the fate of anti-sense oligonucleotides and siRNA can be followed in real time in situ. Since multiple nanoparticles can be arrayed to achieve better signal averaging and extended dynamic range, the amount of protein specifically bound to DNA sequences can be inferred from the footprinting data. This in turn could allow measurement of transcriptome mapping and transcriptional factor binding activity, all in high throughput and multiplexed fashion. The platform here can also be expanded to study different DNA structures and monitor DNA structure change dynamics (Sonnichsen et al. (2005) *Nat Biotechnol* 23: 741-745 (2005)). The novel technology developed and described herein can be used for the detection of other hydrolytic enzymes, such as proteases or glycosylases; or other enzymes that change biomolecule length or charges, such as ligases or kinases. It also provides a high-sensitivity, high-specificity method for enzymatic studies without the need for radioactive or fluorescent labeling. The infinitesimal dimension of a single nanoconjugate also implies a potential large-scale detector array for high-throughput nuclease detections with each individual reaction detectable in a volume less than femto liter.

The foregoing applications are meant to be illustrative and not limiting. Using the teaching provided herein, one of skill will recognize many embodiments for "footprinting" applications.

C) Plasmon Resonance Ruler Collections.

In various embodiments, this invention pertains to collections of nanoplasmonic rulers that can be used, for example for high throughput assays, broad screening systems, microfluidics applications, and the like. The collections typically comprise a plurality of nanoconjugates where different conjugates bear different nucleic acids. The different nanoconjugates are addressed so that they can be distinguished before and/or during and/or after plasmon resonance measurements as describe herein.

In certain embodiments, for example, different nanoconjugates are attached to or otherwise localized in at different regions of a substrate and so they are "spatially addressed". Alternatively the nanoplasmonic conjugates can bear various tags to identify or distinguish different species. The tag can comprise different nanoparticles shapes and/or materials, or different resonance signatures, or can be provided by attached labels, and the like. Methods of tagging collections of moieties are well known to those of skill in the art.

In various embodiments such collections comprise at least 3, preferably at least 5, more preferably at least 10, 20, 25, or 50, and most preferably at least 100, 500, 1000, 5,000, or 10,000 different species.

By way of illustration, in one embodiments it is contemplated to provide a platform comprising an array of the present nanoconjugates for parallel and multiple detection and quantification. In one embodiment, a library of target sequences is provided in array format thereby allowing a user to map and quantify multiple target sequences simultaneously. For example, an oligonucleotide library of transcription factor binding sequences in ssDNA form can be bound to the nanoparticle to comprise the nanoconjugate library, with built in redundancy of sequences that bind to the same transcription factor. A transcription factor is provided and allowed to bind to the target sequences in the nanoconjugate library, whereby upstream transcription factor activity and regulation by DNA sequence can be measured using the present SPR detection methods. This is often more meaningful to a researcher than observing endpoint readouts of downstream mRNA expression.

II. Plasmon Resonance Rulers (Nanoconjugates) Composition and Fabrication.

In various embodiments, the plasmon resonance rulers (nanoparticles conjugates) comprise a single- or double-stranded nucleic acid conjugated to a nanoparticles. In various embodiments the nucleic acid is directly attached to the nanoparticles (e.g., through a covalent bond), while in other embodiments, the nucleic acid is attached to the nanoparticles by a linker.

In various embodiments the nanoparticle is comprised of a metal or a semiconductor material. Nanoparticles useful in the practice of the invention include, but are not limited to nanoparticles comprises of a metal (e.g., gold, silver, copper, tungsten, platinum, titanium, iron, manganese, and the like, or oxides or alloys thereof), a semiconductor material (e.g., CdSe, CdS, and CdS or CdSe coated with ZnS, and the like), multi-layers of metals and/or metal alloys, and/or metal oxides or nitrides, a polymer, carbon nanomaterials, magnetic (e.g., ferromagnetite) colloidal materials, and the like. In certain embodiments nanoparticles comprises one or more of the following: tungsten, tantalum, niobium, Ga, Au, Ag, Cu, Al, Ta, Ti, Ru, Ir, Pt, Pd, Os, Mn, Hf, Zr, V, Nb, La, Y, Gd, Sr, Ba, Cs, Cr, Co, Ni, Zn, Ga, In, Cd, Rh, Re, W, Mo, and oxides, alloys, mixtures, and/or nitrides thereof. Other nanoparticles useful in the practice of the invention include, but are not limited to ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs.

In certain embodiments the size of the nanoparticles is preferably from about 5 nm to about 300 nm (mean diameter), preferably from about 5 to about 150 nm (mean diameter), more preferably from about 10 to about 50 nm, most preferably from about 20 to about 30 nm. The size of the nanoparticles can be varied as required by their particular use or application.

Suitable nanoparticles include, but are not limited to nanospheres, nanorods, nanoscrescents, nanotubes, nanopyramids, nanowires, nanohorns, nanotubes, nanopyramids, nanotetrepods, single- or multi-layered nanodisks, nanohorns, and the like. Essentially any shape nanoparticles can be used in certain embodiments. The nanoparticles can be solid, single-layered, or multi-layered, or core-shell structures.

In certain embodiments the nanoparticle is a gold and/or silver nanoparticle because the shift in plasmon resonance wavelengths shift in response to changes in the immediate environment of these nanoparticles, thereby facilitating their detection using scattering or absorption spectroscopy.

In certain embodiments this invention contemplates the use of multi-meric nanoparticles (e.g., gold and/or silver nanoparticle dimmers). Such multimeric nanoparticles are known to those of skill in the art (see, e.g., Sonnichsen et al. (2005) Nat Biotechnol 23, 741-745, which is incorporated herein by reference).

Methods of fabricating nanoparticles are well known to those of skill in the art. Such methods include, but are not limited to combustion synthesis (e.g., using an oxidizer (e.g., metal salt) and a fuel (e.g., organic compounds) in a redox reaction), evaporation/condensation (EC) generators, spray pyrolysis (e.g., plasma processing and powder spray), liquid phase methods using solution chemistry such as supercritical fluids, chemical reduction, or chemical oxidation, mechanical alloying, template methods (e.g., forming nanoparticles within small voids or areas in template materials such as zeolites, pillared clays, nanoporous membranes, inverse micelles, and the like (see, e.g., U.S. Pat. Nos. 7,212,284, 7,204,999, 7,147,712, 7,128,891, 6,972,046, 6,688,494, 5,665,277 which are all incorporated herein by reference, and PCT Patent Application No: WO/2007/024323, which is incorporated herein by reference). The production of nanohorns is described, e.g., by Berber et al. (2000) Physical Review B, 62(4): R2291-2294, while the production of nanofibers is described, for example in U.S. Pat. Nos. 6,706, 248, 6,485,858, which are incorporated herein by reference. See also, Fedlheim and Colby (2001) Metal Nanoparticles: Synthesis Characterization & Applications, Marcel Dekker, Inc., N.Y.; Baraton (2002) Synthesis, Functionalization and Surface Treatment of Nanoparticles, American Scientific Publishers; Fendler (1998) Nanoparticles and Nanostructured Films: Preparation, Characterization and Applications, Wiley-VCH, N.Y.; and the like.

In certain embodiments the nanoparticles are synthesized in surfactant systems. Such surfactant-based methods are well known to those of skill in the art.

More generally, in certain embodiments, nanoparticles can be formed on the reduction of metallic salts by organic solvents (e.g., ethanol) to form metal colloids (see, e.g., Hirai et al. (1979) J. Macromol. Sci. Chem., A13: 727; Hirai et al. (1976) Chem. Lett., 905; Toshima and Yonezawa (1992) Makromol. Chem., Macromol. Symp., 59: 281; Wang and Toshima (1997) J. Phys. Chem., 97: 11542, and the like). One illustrative approach is described by Pastoriza-Santos and Liz-Marzan (2000) Pure Appl. Chem., 72(1-2): 83-90. In their approach, $Ag^+$ ions are reduced by N,N-dimethylformamide (DMF) in the presence or absence of a stabilizing agent. The reaction leads to the formation of either thin films of silver nanoparticles electrostatically attached onto surfaces, or stable dispersions of silver nanoparticles.

In another illustrative approach, magnetite nanoparticle materials can be made by mixing iron salt with alcohol, carboxylic acid and amine in an organic solvent and heating the mixture to 200-360 C. The size of the particles can be controlled either by changing the iron salt to acid/amine ratio or by coating small nanoparticles with more iron oxide. Magnetite nanoparticles in the size ranging from 2 nm to 20 nm with a narrow size distribution can readily be obtained. The method can easily be extended to other iron oxide based nanoparticle materials, including $MFe_2O_4$ (where M is for example Co, Ni, Cu, Zn, Cr, Ti, Ba, Mg, and the like) nanomaterials, and iron oxide coated nanoparticle materials. The method also leads to the synthesis of iron sulfide based nanoparticle materials by replacing alcohol with thiol in the reaction mixture. The magnetite nanoparticles can be oxidized to $\gamma$-$Fe_2O_3$, or -$Fe_2O_3$, or can be reduced to bcc-Fe nanoparticles, while iron oxide based materials can be used to make binary iron based metallic nanoparticles, such as CoFe, NiFe, and $FeCoSm_x$ nanoparticles (see, e.g., U.S. Pat. No. 7,128, 891, which is incorporated herein by reference).

One method of producing gold nanoparticles involves mixing a gold salt solution with an adsorbent. Gold in the form of complexes is adsorbed onto the surface of the adsorbent. The gold-loaded adsorbent, after being separated from the solution by screening, filtration, settling or other methods, is ashed to form ashes. The ashes contain gold nanoparticles and impurities such as oxides of sodium, potassium and calcium. The impurities can be removed by dissolution using dilute acids. The relatively pure gold nanoparticles are obtained after the impurities are removed. Activated carbon or gold-adsorbing resin can be used as the adsorbent. Silver or platinum group metal nanoparticles can also readily be produced by this method (see, e.g., U.S. Pat. No. 7,060,121, which is incorporated herein by reference).

In still another approach, nanoparticles, can be formed using laser pyrolysis. Conventional laser pyrolysis processes, often called photothermal processes, are well known to those of skill in the art (see, e.g., U.S. Pat. Nos. 5,958,348, 3,941, 567, 6,254,928, which are incorporated herein by reference, and the like). In this process, a radiation absorber or other precursor gaseous species absorbs energy (e.g., laser light, which results in the heating of the materials in a reaction zone causing thermally driven chemical reactions between the chemical components in the reaction zone. Typically, laser pyrolysis processes employ a precisely defined hot zone (typically 1000~1500° C.) generated, e.g., by a laser beam passing through a chemical vapor zone, in which gases thermally react to form the desired nanoscale particulate materials. The absence of wall in contact with the hot zone eliminates any contamination.

The materials formed in the pyrolytic reaction leave the hot zone typically driven by gravity or gas flow. The materials are rapidly cooled/quenched thereby forming nanoparticles with a very uniform distribution of sizes and shapes. In typical embodiments, a carbon dioxide ($CO_2$) laser is used to heat the gas molecules directly by light absorption. Another advantage of using a laser is its narrow spectral width, which allows efficient coupling between the light and the molecular precursor that has exact wavelength of absorption (over 15% of laser power consumed). The technology has been used to produce various nanosize materials from metals, metal carbides, metal nitrides and metal oxides (see, e.g., Haggerty et al. (1981) pp 165-241 In: Laser Induced Chemical Processes, edited by J. J. Steinfeld; Bi et al. (1993) J. Mater. Res., 8(7): 1666-1674; Bi et al. (1995) J. Mater. Res. 10(11): 2875-2884; Curcio et al. (1990) Applied Surface Science, 46: 225-229; Danen et al. (1984) SPIE, 458: 124-130; Gupta et al. (1984) SPIE, 458: 131-139; U.S. Pat. Nos. 5,958,348, 6,225,007, 6,200,674, 6,080,337, and the like).

Numerous nanoparticles in various size ranges are also commercially available (see, e.g., Sun Nano, Freemont, Calif.; Northern Nanotechnologies, Toronto, Canada; and the like).

In certain embodiments the nanoparticles are modified to improve solubility, dispersibility, e.g., in aqueous solutions. Thus, for example, in certain embodiments the nanoparticles are modified with a phosphine layer or other layer.

In various embodiments the nanoparticles or the nucleic acids, or both, can be functionalized to facilitate attachment of the nucleic acids to the nanoparticles. Such methods are known in the art. For instance, nucleic acids (e.g., oligonucleotides) functionalized with alkanethiols at their 3'-termini or 5'-termini readily attach to gold nanoparticles (see, e.g., Whitesides (1995) Proceedings of the Robert A. Welch Foundation 39th Conference On Chemical Research Nanophase Chemistry, Houston, Tex., pages 109-121). Mucic et al. (1996) *Chem. Commun.* 555-557 describes a method of attaching 3' thiol DNA to flat gold surfaces and this method can readily be used to attach nucleic acids to nanoparticles).

In certain embodiment, the methods to functionalize the nanoparticles as described infra can be used to functionalize the nanoparticles. In one embodiment, silica coated particles are functionalized using amino-silane molecules to functionalize the silica surface with amines. In certain embodiments, the nanoparticles are phosphine-functionalized as described in the Examples herein. In another embodiment, the nucleic acids are bound to the nanoparticles using sulfur-based functional groups. U.S. patent application Ser. Nos. 09/760,500 and 09/820,279 and international application nos. PCT/US01/01190 and PCT/US01/10071 describe oligonucleotides functionalized with a cyclic disulfide which are useful in practicing this invention, and are hereby incorporated by reference. The cyclic disulfides preferably have 5 or 6 atoms in their rings, including the two sulfur atoms. Suitable cyclic disulfides are available commercially or may be synthesized by known procedures. The reduced form of the cyclic disulfides can also be used.

In one embodiment, the oligonucleotides have covalently bound thereto, a moiety comprising a functional group which can bind to the nanoparticles. The moieties and functional groups are those that allow for binding (e.g., by chemisorption, covalent, or ionic bonding) of the nucleic acids to nanoparticles. For instance, oligonucleotides having an alkanethiol, an alkanedisulfide or a cyclic disulfide covalently bound to their 5' or 3' ends can be used to bind the oligonucleotides to a variety of nanoparticles, including, but not limited to gold nanoparticles. Methods of attaching oligonucleotides to nanoparticles are further described in U.S. patent application Ser. No. 10/877,750, published as US20050037397, also incorporated herein by reference.

The alkanethiol method can also be used to attach nucleic acids to metal, semiconductor and magnetic colloids and to the other nanoparticles listed above. Other functional groups for attaching oligonucleotides to solid surfaces include, but are not limited to phosphorothioate groups (see, e.g., U.S. Pat. No. 5,472,881 for the binding of oligonucleotide-phosphorothioates to gold surfaces), substituted alkylsiloxanes (see, e.g. Burwell (1974) *Chemical Technology,* 4: 370-377 and Matteucci and Caruthers (1981) *J. Am. Chem. Soc.,* 103: 3185-3191 for binding of oligonucleotides to silica and glass surfaces, and Grabar et al. (1995) *Anal. Chem.,* 67: 735-743 for binding of aminoalkylsiloxanes and for similar binding of mercaptoaklylsiloxanes).

Nucleic acids (e.g., oligonucleotides) terminated with a 5' thionucleoside or a 3' thionucleoside can also be attached to solid surfaces. The following references describe other methods which may be employed to attached oligonucleotides to nanoparticles: Nuzzo et al., (1987) *J. Am. Chem. Soc.,* 109: 2358 (disulfides on gold); Allara and Nuzzo, (1985) *Langmuir,* 1: 45 (carboxylic acids on aluminum); Allara and Tompkins (1974) *J. Colloid Interface Sci.,* 49: 410-421 (carboxylic acids on copper); Iler (1979) *The Chemistry Of Silica,* Chapter 6, (Wiley) (carboxylic acids on silica); Timmons and Zisman (1965) *J. Phys. Chem.,* 69: 984-990 (carboxylic acids on platinum); Soriaga and Hubbard (1982) *J. Am. Chem. Soc.,* 104: 3937 (aromatic ring compounds on platinum); Hubbard (1980) *Acc. Chem. Res.,* 13: 177 (sulfolanes, sulfoxides and other functionalized solvents on platinum); Hickman et al. (1989) *J. Am. Chem. Soc.,* 111: 7271 (isonitriles on platinum); Maoz and Sagiv (1987) *Langmuir,* 3: 1045 (silanes on silica); Maoz and Sagiv (1987) *Langmuir,* 3: 1034 (silanes on silica); Wasserman et al. (1989) *Langmuir,* 5: 1074 (silanes on silica); Eltekova and Eltekov (1987) *Langmuir,* 3: 951 (aromatic carboxylic acids, aldehydes, alcohols and methoxy groups on titanium dioxide and silica); Lec et al. (1988) *J. Phys. Chem.,* 92: 2597 (rigid phosphates on metals).

In one embodiment, the reactive group can tethered to the nanoparticle using methods described by Alivisatos et al. (1996) *Nature* 382: 609-611 (1996); Zanchet et al. (2001) *Nano Lett* 1: 32-35 (2001); Taton et al. (2000) *Science* 289: 1757-1760, and Storhoff et al. (1998) *J. Am. Chem. Soc.* 120: 1959-1964, all of which are hereby incorporated by reference. In one preferred embodiment, the reactive group is a thiol group.

In certain embodiments, the nanoconjugate is comprised of 1, 10, 100, 1000, 10,000, up to 100,000 oligonucleotides tethered to the nanoparticle. In certain preferred embodiments, the nanoconjugate is comprised of about 100 oligonucleotides per particle.

Essentially any nucleic acid (single- or double-stranded) can be used in the nanoconjugates of this invention. In certain embodiments the nucleic acids range in length from about 5 to about 500 nucleotides (or base pairs for double stranded molecules), preferably from 5 to about 400, 300, or 200 nucleotides (or base pairs), more preferably from about 10, 5, 20, 25, 30, or 40 nucleotides (or base pairs) to about 150, 100, 80, or 60 nucleotides (or base pairs).

The nucleic acids can be naturally occurring (e.g., isolated fragments), amplified (e.g., PCR amplified), recombinantly expressed, or chemically synthesized. In certain embodiments the nucleic acid comprises a synthetic oligonucleotide ranging from about 20 to about 200 nucleotides (bp) in length, preferably about 40 to about 100 nucleotides (bp) in length, more preferably about 50 to about 60 bp in length, optionally having a reactive group on one end to tether the oligonucleotide to the nanoparticle.

In one preferred embodiment, the oligonucleotide sequence can be any sequence. In one embodiment, the sequence is: Thiol-AAAGGATCCA AGCTTGAATT CCTCG-X-AGAGATCTGTCGACGATATCGGTACCAAA (SEQ ID NO:15), where X is any target DNA sequence or feature inserted. The oligonucleotide features restriction sites at about 10, 20, 25, 30, 40, and/or 50 bp, thus facilitating insertion and digestion sites at distance markers of 10 bp. In one embodiment, the target binding sequence begins about half of the length of the oligonucleotide. For example, in FIG. 15B, the transcription factor sequence begins at 25 bp in a 54 bp oligonucleotide.

Nucleic acids (e.g., oligonucleotides) of defined sequences are used for a variety of purposes in the practice of the invention, e.g., as described above. Methods of making nucleic acids (e.g., oligonucleotides) of a predetermined sequence are well known to those of skill in the art (see, e.g., Sambrook et al. (1989) *Molecular Cloning: A Laboratory Manual* (2nd ed.) and Eckstein (ed.) (1991) *Oligonucleotides and Analogues,* 1st Ed. (Oxford University Press, New York). In certain embodiments solid-phase synthesis methods are preferred for both oligoribonucleotides and oligodeoxyribonucleotides (the well-known methods of synthesizing DNA are also useful for synthesizing RNA). In certain embodiments oligoribonucleotides and oligodeoxyribonucleotides can also be prepared enzymatically (e.g., in vitro, in recombinant expression systems in amplification systems, and the like). The nucleic acid can be double-stranded (ds) or single-stranded (ss) DNA, RNA, or DNA/RNA hybrid.

III. Detection

In various embodiments the nanoconjugate plasmon resonance signal is detected using surface plasmon resonance (SPR) methods. Typically, the nucleic acid nanoconjugate is immobilized (e.g., magnetically immobilized, electrostatically immobilized, chemically immobilized, adsorbed, etc.) on a substrate appropriate for SPR. One illustrative substrate is an ultra-clean thin glass slide, but the substrate need not be so limited.

In certain embodiments the scattering image and spectrum of nanoconjugates are acquired using a dark-field microscopy system with a true-color imaging camera and a spectrometer. In one illustrative embodiments, the microscopy system consisted of a Carl Zeiss Axiovert 200 inverted microscope (Carl Zeiss, Germany) equipped with a darkfield condenser (1.2<NA<1.4), a true-color digital camera (CoolSNAP cf, Roper Scientific, NJ), and a 300 mm focal-length and 300 grooves/mm monochromator (Acton Research, MA) with a 1024×256-pixel cooled spectrograph CCD camera (Roper Scientific, NJ). A 2 µm wide aperture was placed in front of the entrance slit of the monochromator to keep only a single nanoparticle in the region of interest. After photobleaching the fluorescence, the true-color scattering images of Au-DNA nanoconjugates were taken using a 60× objective lens (NA=0.8) and the true-color camera with a white light illumination from a 100 W halogen lamp.

The scattering spectra of Au-DNA nanoconjugates were taken using the same optics, but they were routed to the monochromator and spectrograph CCD. Raw spectra were normalized with respect to the spectrum of a non-resonant nanoparticle (i.e., polystyrene) after the background subtraction. In the real-time spectroscopy experiments, the nanoparticle-immobilized glass slide was mounted on a transparent ITO heater with an external thermostat. The immobilized nanoparticles were immersed in a drop of buffer solution which also served as the contact fluid for the dark-field condenser. The distance between the condenser and nanoparticles was 1~2 mm. The endonuclease enzymes with buffer solution were loaded by pipette into the contact fluid and the continuous spectrum acquisition started simultaneously. The microscopy system was completely covered by a dark shield, which prevented ambient light interference and serious evaporation of the buffer solution.

In one illustrative embodiment, real-time plasmon resonance sensing of endonuclease reactions of the DNA-nanoparticle nanoconjugate are carried out as described herein in the examples.

IV. Kits

In another embodiment this invention provides kits for practice of the methods of this invention. In certain embodiments the kits comprise a container containing a nanoplasmonic ruler of this invention. The ruler comprises a plurality of restriction sites and can be used to calibrate a detection system for measuring length changes of nucleic acids. In certain embodiments the kits comprise a container containing nanoplasmonic rulers comprising nucleic acids designed with sites for insertion of particular nucleic acid sequences, e.g., as described herein, or for probing nucleic acid samples for particular features (e.g., polymorphisms, insertions, deletions, etc.) and/or for detecting the presence of and/or localizing one or more nucleic acid binding proteins (e.g., transcription factors, enzymes, and the like). In certain embodiments the nanoconjugates comprise a collection of nanoconjugates either chemically addressed, or spatially addressed on a substrate, or separated with different species in different containers.

The kits optionally include nucleic acid binding proteins, and/or endonucleases, and/or exonucleases as described herein.

In addition, the kits optionally include labeling and/or instructional materials providing directions (i.e., protocols) for the practice of the methods described herein. Preferred instructional materials describe the use of one or more nanoconjugates as described herein for the calibration of an SPR system for measuring nucleic length changes and/or for performing any of the methods described herein.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Figure 2A:
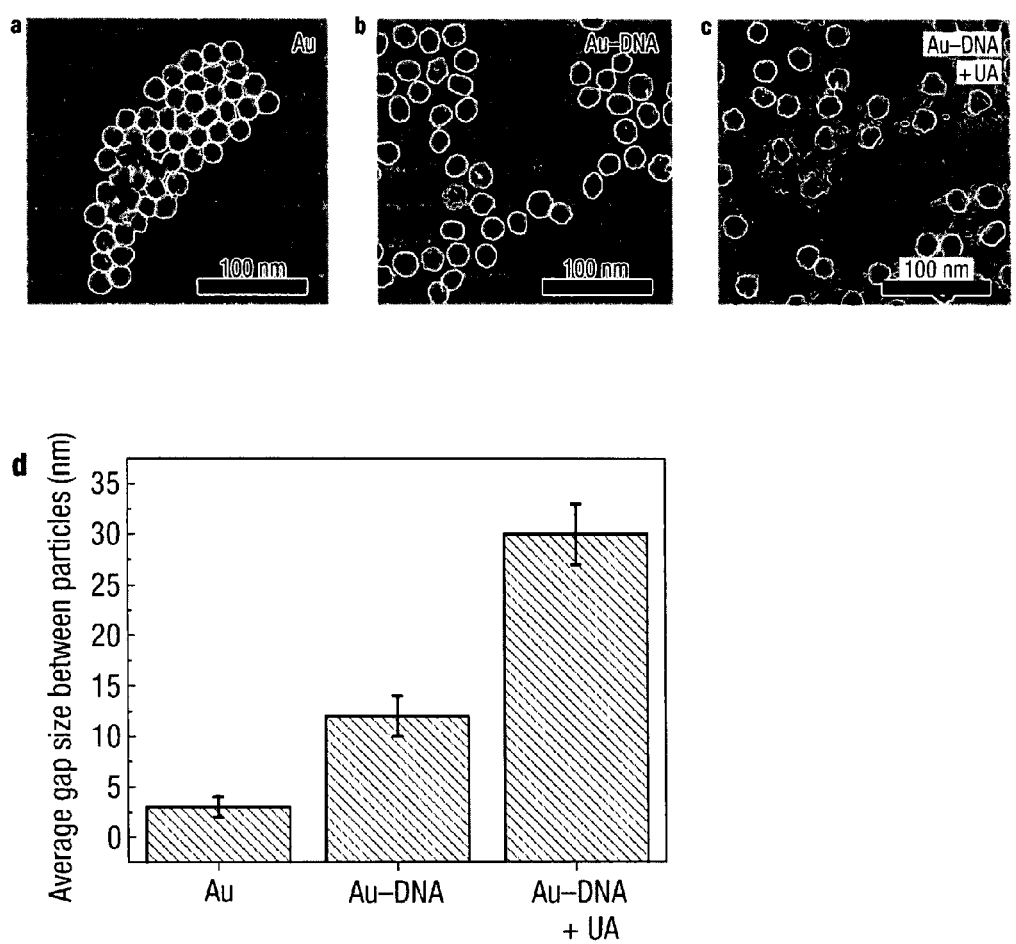
FIGS. 2A-2D show the DNA conjugation red-shifted plasmon resonance peak of the molecular ruler.
Figure 2B:
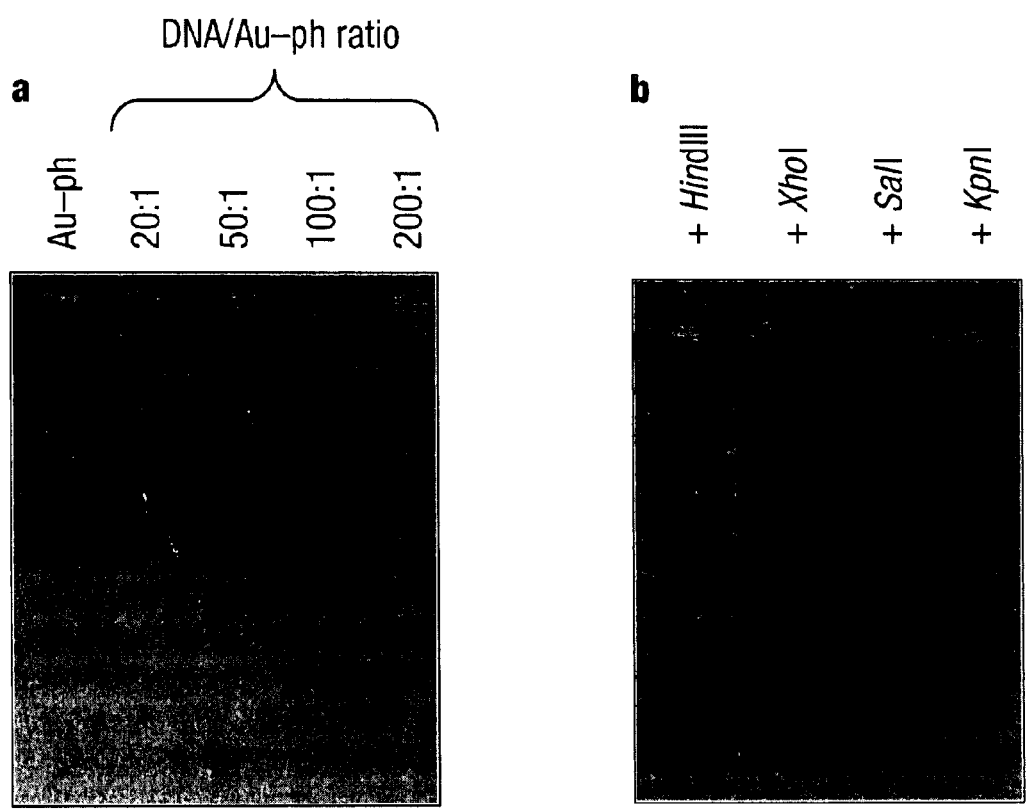

A Nanoplasmonic Molecular Ruler for Measuring Nuclease Activity and DNA Footprinting In this example we designed a nanoplasmonic molecular ruler, with a 54-bp double-stranded DNA (dsDNA) as the enzymatic substrate and calibration standard, conjugated to a 20-nm Au nanoparticle (FIGS. 1A, 1B, and 2A, panels a-c). The dsDNA contained cleavage sites for the endonucleases HindIII, XhoI, SalI and KpnI, centered at nucleotide positions 12, 24, 36 and 48, respectively (FIG. 1B). The surface density of dsDNA on the Au nanoparticles was controlled by their concentration ratio during immobilization. A 100:1 DNA/Au ratio was found to be the best compromise to preserve the natural extension of dsDNA (FIG. 2A), while allowing accessibility to the nuclease (Parak et al. (2003) *Nano Lett.* 3: 33-36) (FIG. 2B). The surface modification of Au nanoparticles with dsDNA was confirmed by transmission electron microscopy (TEM) (FIG. 2A) and electrophoresis (FIG. 2B, panel a).

Figure 2C:
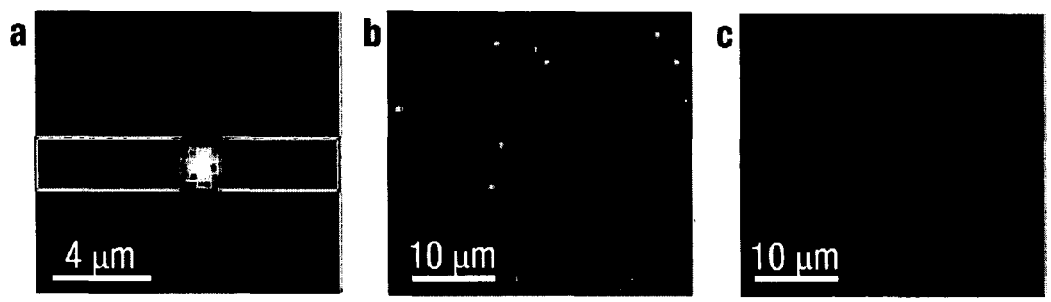
Figure 2D:
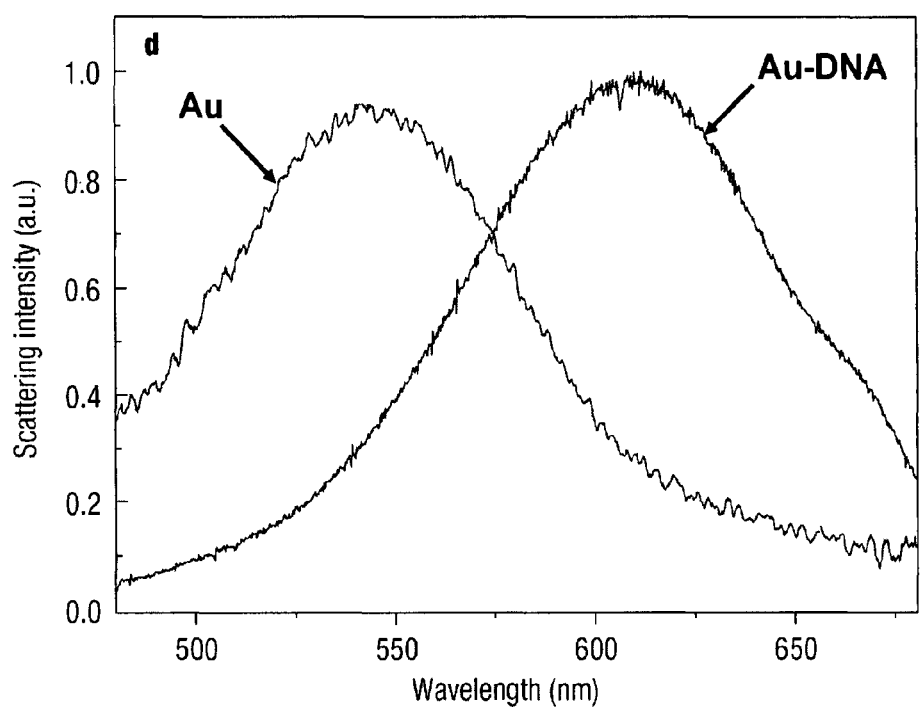
Figure 7:
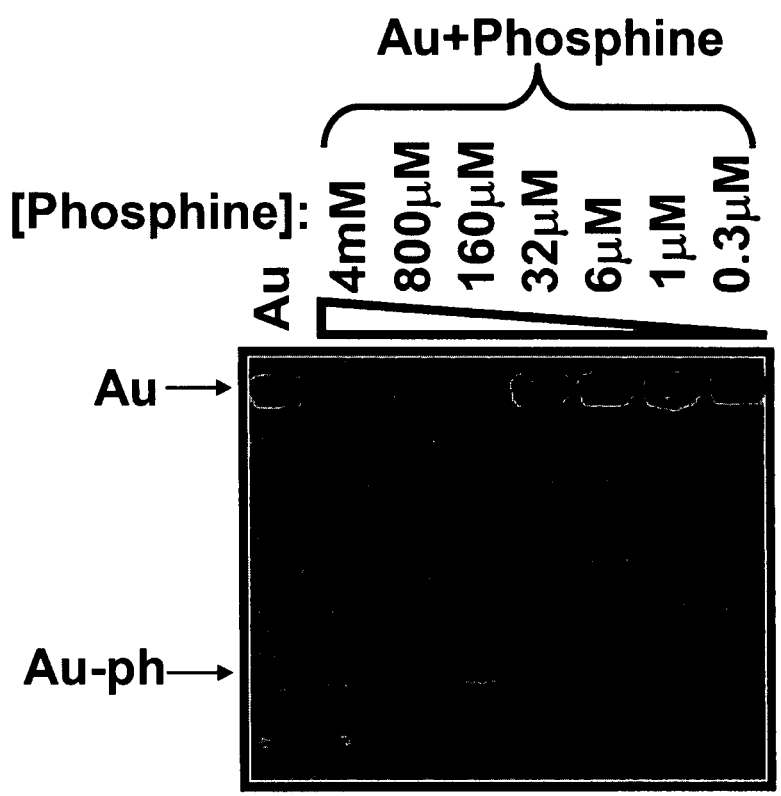
FIG. 7 shows gel electrophoresis of nanoconjugates. Shown are: (1) Au-phosphine (Au-ph) nanoconjugates in different phosphine/Au ratios. The Au nanoparticles were stabilized through surface exchange with Bis(p-sulfonatophenyl) phenylphosphine (phosphine) to prevent aggregations. Left lane is a control of Au nanoparticle without phosphine surfactants. For purpose of simplifying the writing, the Au-ph is called Au in Example 1, since all the Au nanoparticles used in the study have the phosphine surfactant coating.

The scattering images and spectra of individual nanoconjugates were acquired using a dark-field microscopy system with a true-color imaging charge-coupled device (CCD) camera and a spectrometer (FIG. 2C, panel a). Interestingly, Au (FIG. 2C, panel b), which carries no DNA but a phosphine surfactant (see FIG. 7), and Au-DNA (FIG. 2C, panel c) exhibit different colors in yellow and red, respectively. The attachment of DNA seems to red-shift the peak plasmon resonance wavelength of the Au nanoparticle by 67 nm (FIG.

Figure 3A:
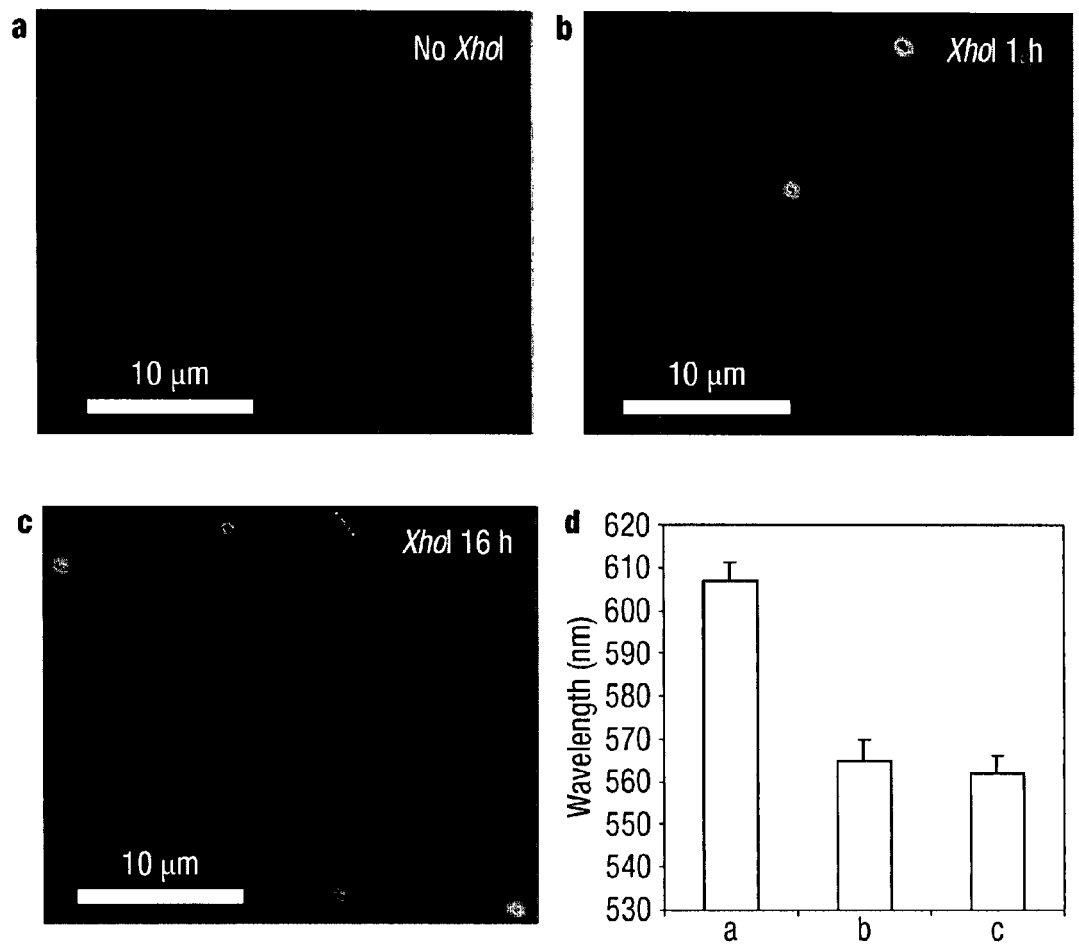
FIGS. 3A and 3B show endonuclease activity measurement with ruler.
Figure 3B:
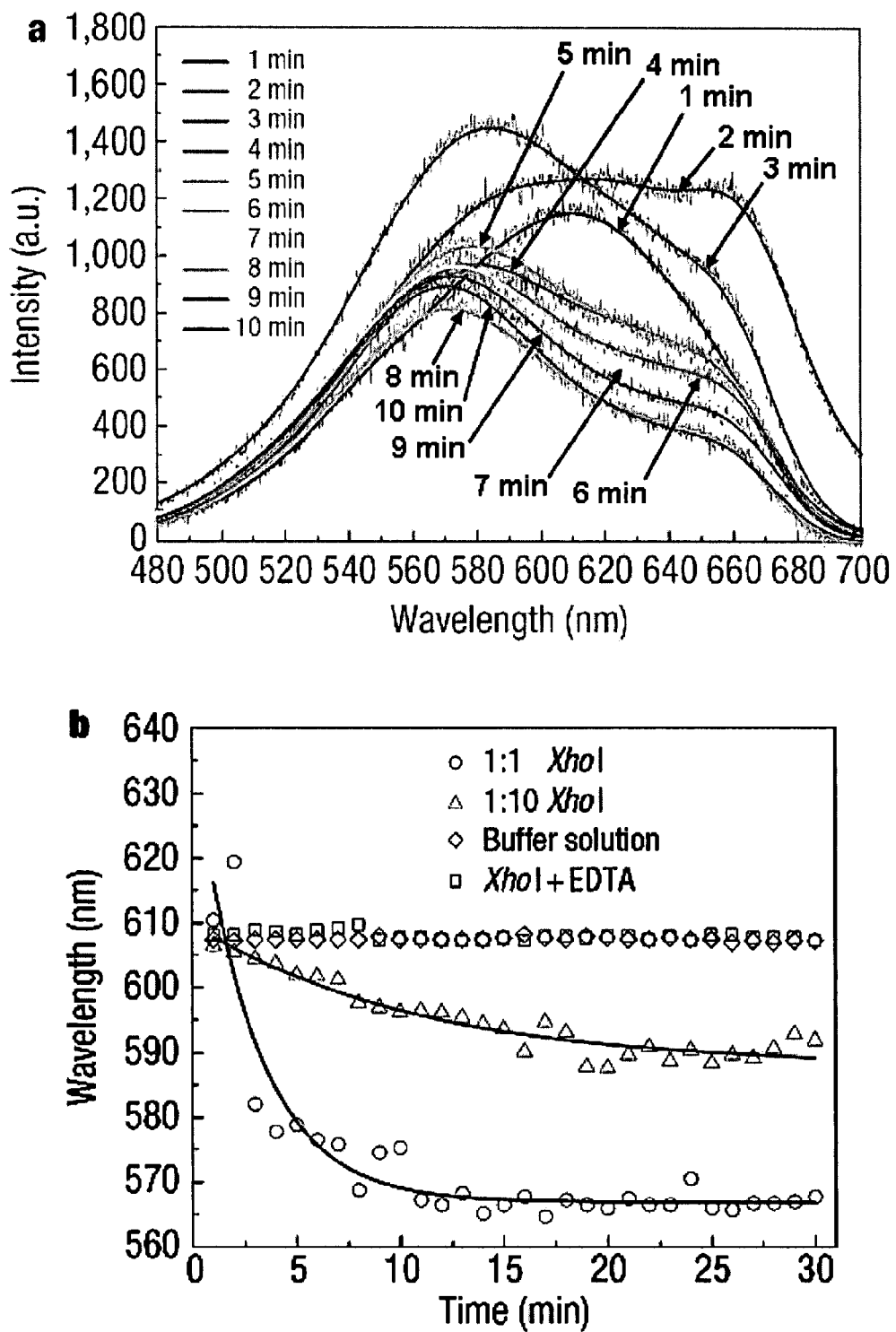
Figure 8:
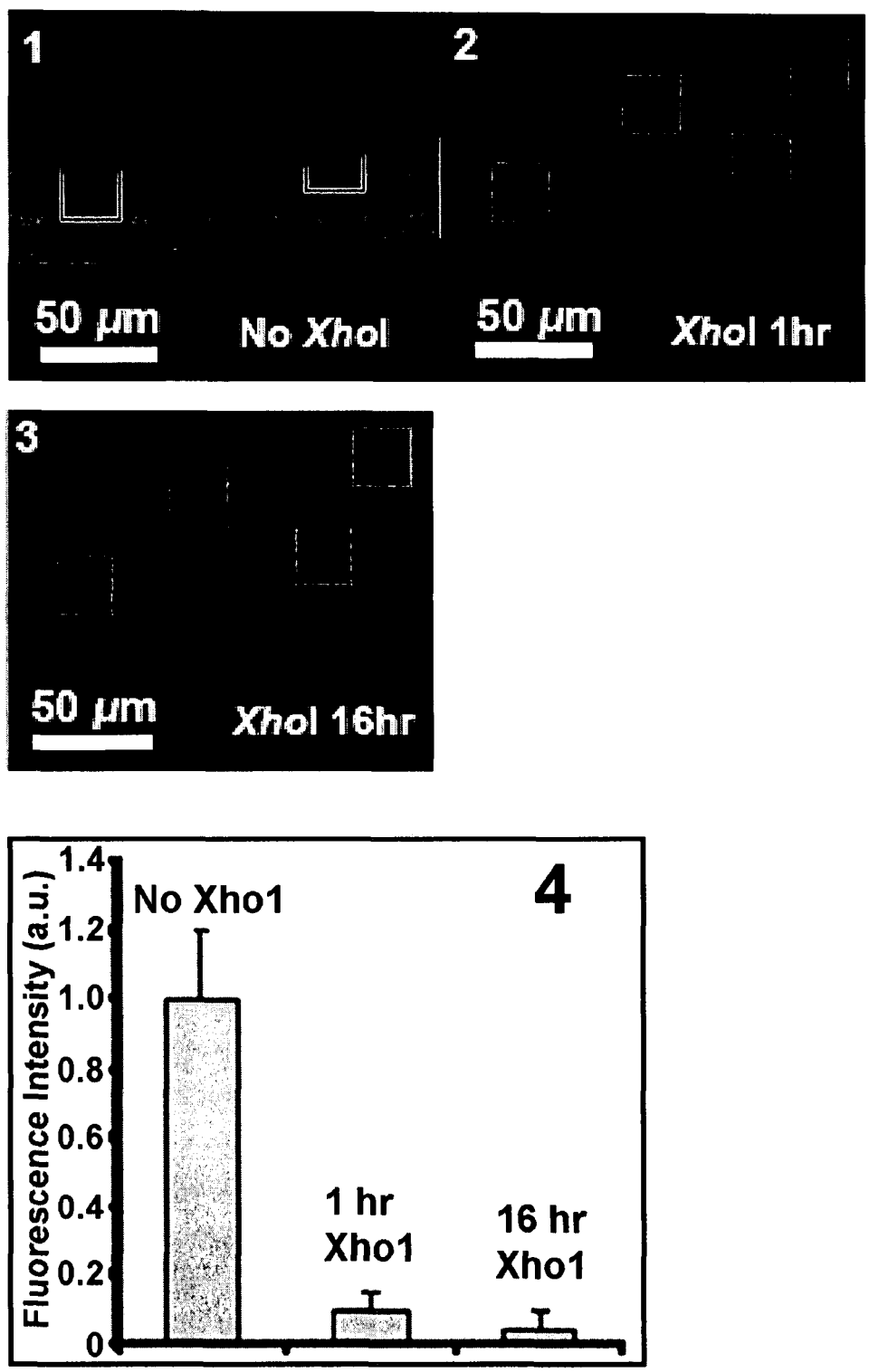
FIG. 8, panels 1-4, show the confirmation of endonuclease cleavage. The same reactions as in FIG. 3A were carried out and imaged with fluorescence imaging. Shown are: fluorescence images of Au-DNA nanoconjugates (panel 1) before, (panel 2) 1 hr and (panel 3) 16 hr after the cleavage reaction by enzyme XhoI. The fluorescence intensities at four different areas (squares) in each case were measured and the statistics of the fluorescence intensities are shown in (panel 4) with the average fluorescence intensity of the single Au nanoconjugates in the above three cases. Note the full length of the complete dsDNA (~20 nm) is much longer than the effective Forster transfer distance (<10 nm), and thus the FITC fluorophore at distal end of DNA was not quenched. The FITC fluorophore was detached from the Au nanoparticles and diffused into the buffer solution after the DNA cleavage, so that the overall fluorescence intensity at the image plane (where the Au nanoparticles are) decreased dramatically.

2C, panel d). The ruler provides a new means for studying the kinetics of the nuclease enzymatic reactions. Real-time measurement of endonuclease activity and kinetics for one model endonuclease, XhoI, was demonstrated, and the average plasmon resonance wavelength drops after the XhoI endonuclease reactions due to the loss of 30 bp of dsDNA (FIGS. 3A, 3B, and 8). EDTA-induced inhibition of XhoI reaction can also be visualized (FIG. 3B). The salt concentration change was negligible, as all components were preincubated with the same reaction buffer (FIG. 3B).

Figure 4A:
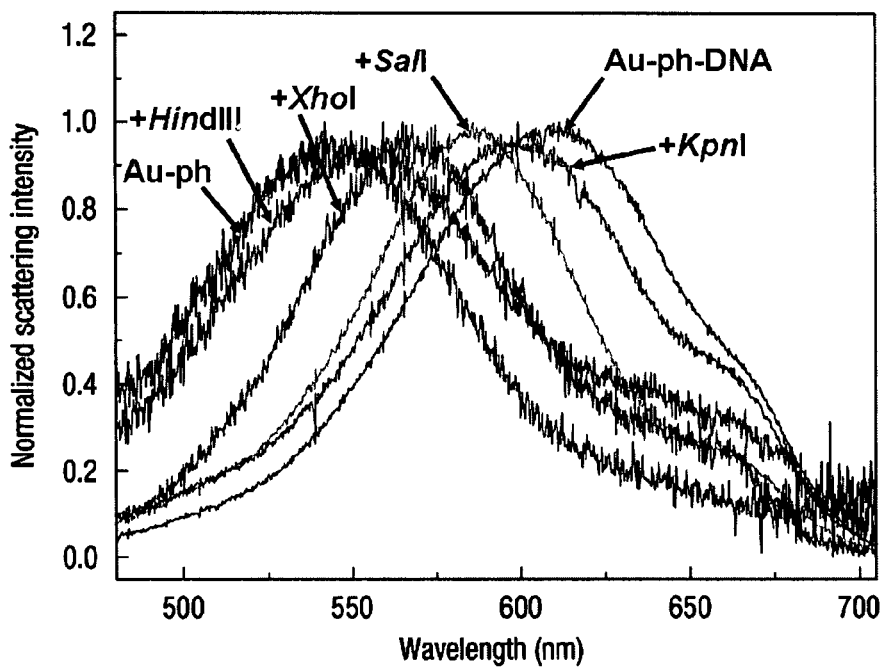
FIGS. 4A and 4B show calibration curve generation by nanoplasmon resonance sensing of multiple enzymes.
Figure 4B:
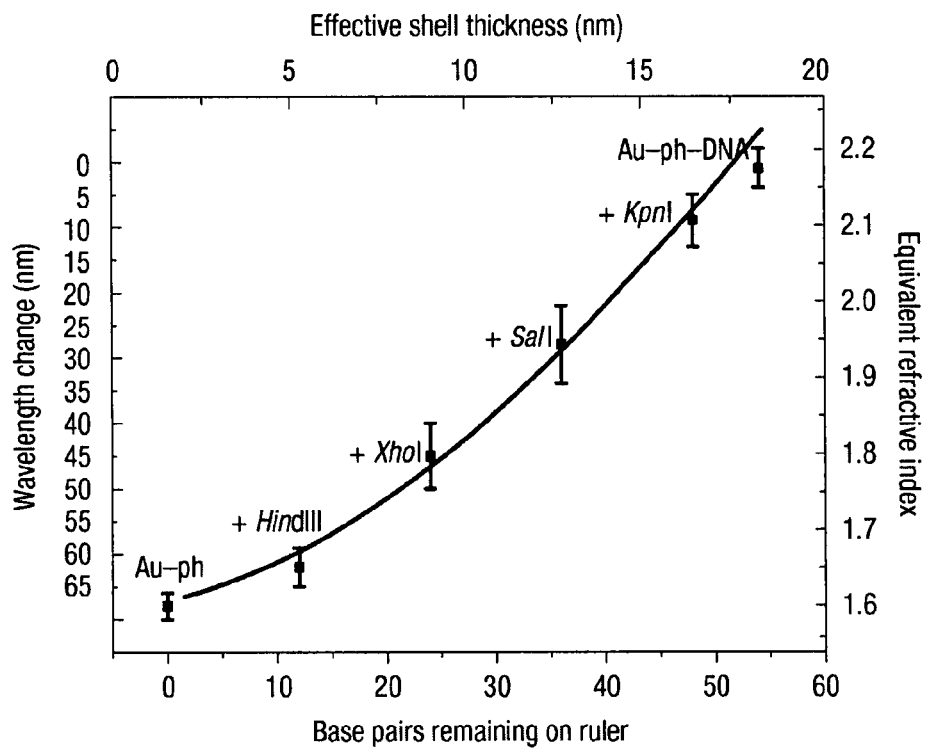
Figure 9:
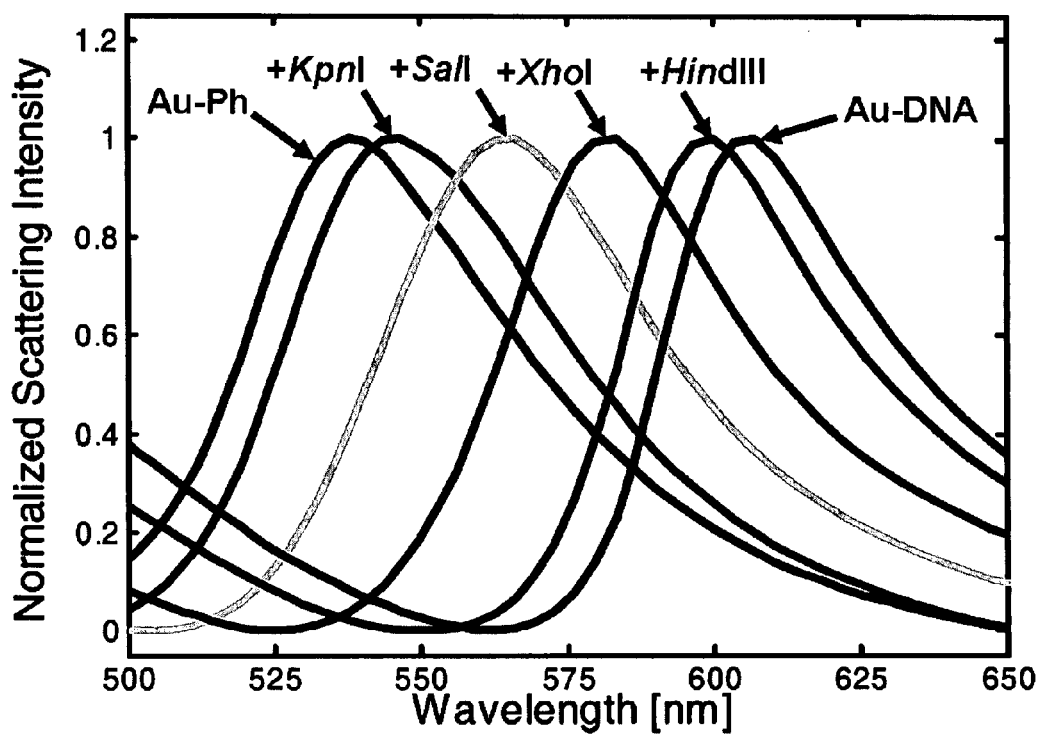
FIG. 9 shows simulated scattering spectra of the Au-DNA nanoconjugates after cleavage by different endonuclease enzymes. The wavelength-dependent dielectric constant of Au is interpolated from the tabulated data by Johnson and Christy (1972) *Phys. Rev. B* 6, 4370-4379. The simulation code is modified from the BHCOAT by Bohren and Huffman, (1983) *Absorption and scattering of light by small particles* (John Wiley & Sons, Inc., New York).

We then focused on the size effect of the attached DNA. In order to investigate whether the nanoplasmonic resonance frequency shift of the Au-DNA nanoconjugate can accurately reflect DNA size change, we artificially produced DNA size standards by endonuclease cleavage. About ten nanoconjugates from each sample were examined spectroscopically in dark field and the average plasmon resonance wavelengths are shown in FIGS. 4A and 4B. Au-DNA nanoconjugates were reacted with KpnI, SalI, XhoI and HindIII, which cleaved the first 6, 18, 30 and 42 bp from the distal end of the full-length dsDNA, respectively. FIG. 4A shows the typical scattering spectra and plasmon resonance wavelengths of Au-DNA nanoconjugates after the 1-hour cleavage reactions. FIG. 4B shows the plasmon resonance spectra of single Au nanoparticles tethered with 0, 12, 24, 36, 48 and 54 bp of dsDNA. The average wavelength blue shifts from the Au-DNA were approximately 67 nm, 62 nm, 45 nm, 28 nm, 10 nm and 0 nm, respectively. The plasmon resonance shift of the nanoparticle corresponded to the change of the dielectric layer around the nanoparticle and is related to the length of the digested dsDNA. Using the Mie scattering calculation for coated Au nanoparticles (Bohren and Huffman (1983) *Absorption and Scattering of Light by Small Particles* (Wiley, New York), the equivalent dielectric constant, or refractive index of the biopolymer shell (dsDNA+phosphine), was obtained (see, FIG. 4B, FIG. 9, and Table 1, below).

the complete dsDNA (~20 nm) is much longer than the effective Förster transfer distance (<10 nm), so the ruler has a longer detection range than the Förster resonance energy transfer.

Figure 5A:
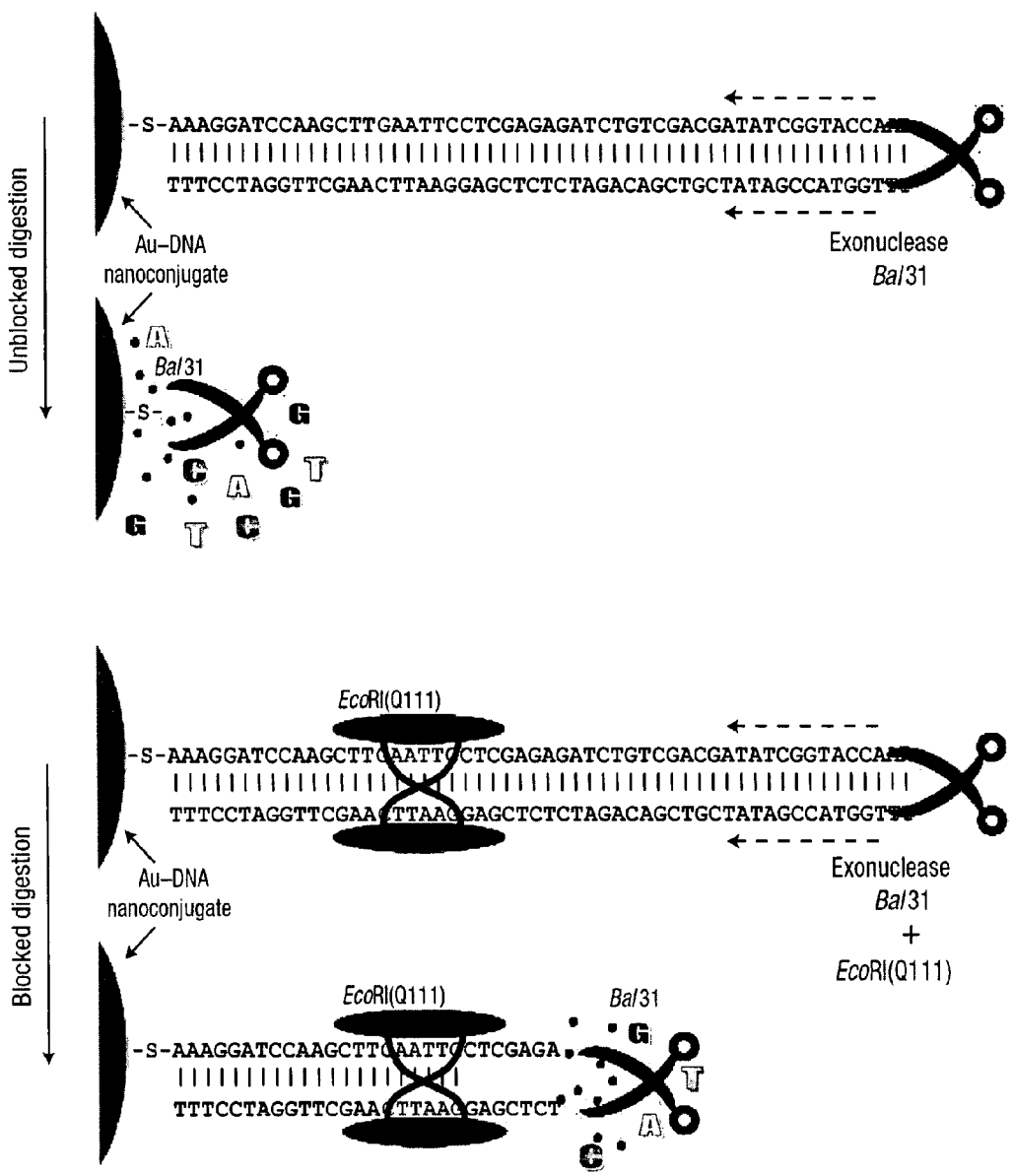
FIGS. 5A-5D illustrate DNA footprinting of Bal31 exonuclease stalled by the EcoRI(Q111) proteins.
Figure 5B:
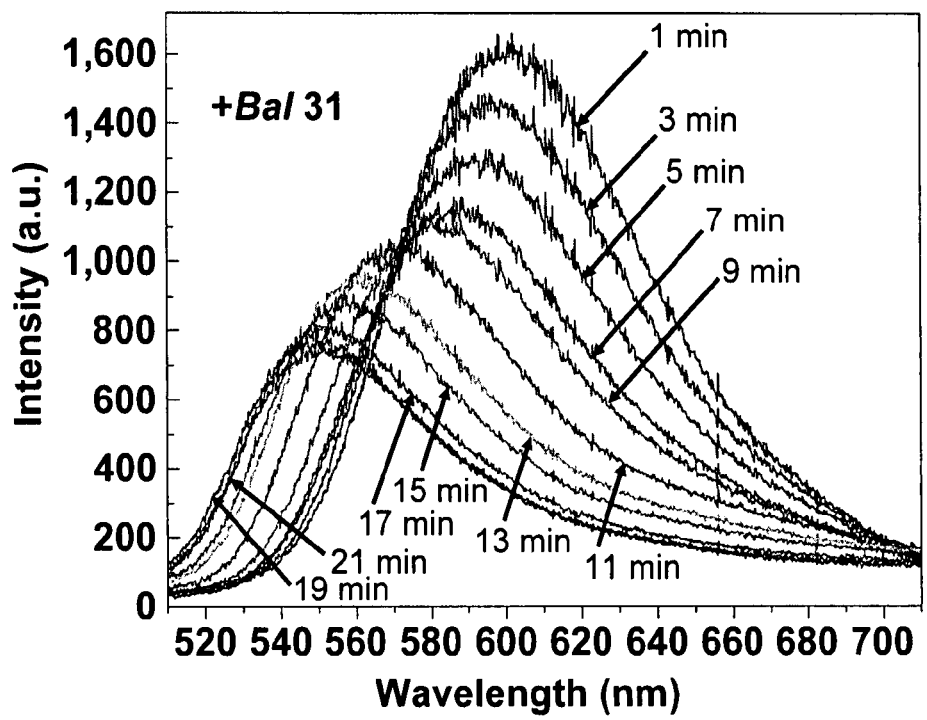
Figure 5C:
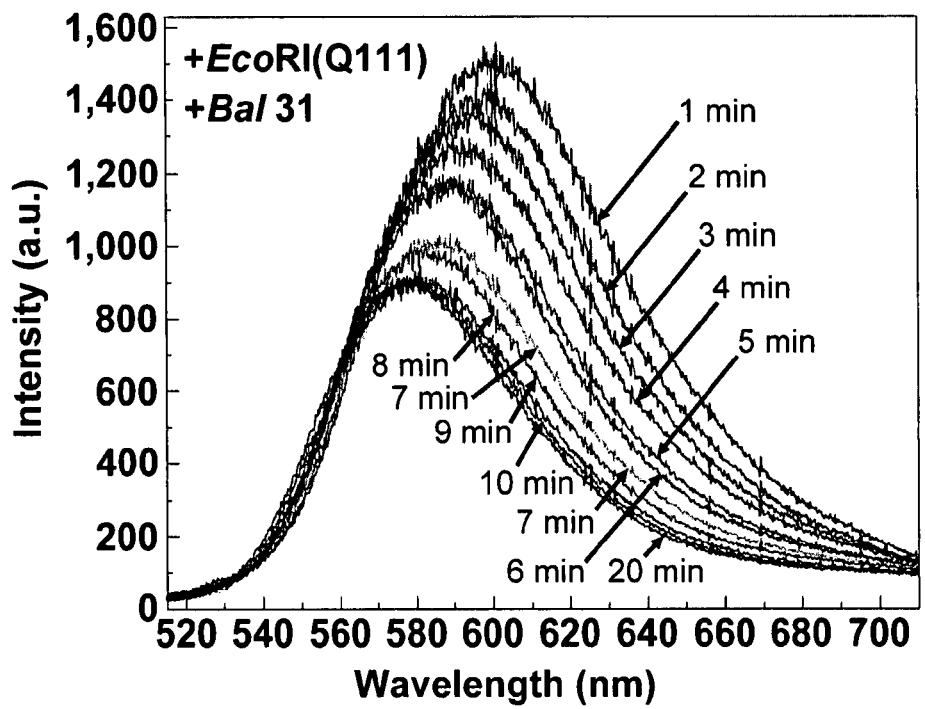

Based on the established correlation curve between the shifts in the plasmon wavelength and the DNA size (FIG. 4B), DNA length in a nuclease reaction could be determined, which allowed us to measure the footprint of DNA-binding proteins. EcoRI(Q111) protein was used as a model protein in exonuclease-based DNA footprinting. EcoRI(Q111) is a cleavage-defective variant of the EcoRI protein with amino acid residue 111 mutated to glutamine (Q). EcoRI(Q111) still maintains specific binding activity to the sequence GAATTC on dsDNA, but does not cleave DNA (King et al. (1989) *Biol. Chem.* 264: 11807-11815; Pavco and Steege (1990) *Biol. Chem.* 265: 9960-9969). EcoRI(Q111) has previously been used to block a transcription elongation complex (Jett et al. (1994) *Proc. Natl. Acad. Sci., USA*, 91: 6870-6874). As depicted in FIG. 5A, EcoRI(Q111) binds to the GAATTC (SEQ ID NO:16) sequence on the Au-DNA nanoconjugates. Subsequently an exonuclease enzyme, Bal31, is introduced to degrade the dsDNA from the untethered end without any specificity. Bal31 exonuclease degrades both 3' and 5' termini of dsDNA (Legerski et al. (1978) *Nucleic Acids Res.* 5: 1445-1464). FIGS. 5B and 5C show the scattering spectra of the Au-DNA nanoconjugate digested by Bal31, without and with the bound EcoRI(Q111), respectively. For the unbound DNA, the plasmon resonance wavelength of the nanoconjugate was blue-shifted ~52 nm by Bal31 in 20 min and stabilized afterwards (squares in FIG. 5D); however, for the DNA bound by the EcoRI(Q111), the plasmon resonance wavelength of the nanoconjugate shifted a maximum of 25 nm before stabilization (circles, FIG. 5D). The corresponding base pair length of the degraded dsDNA was calculated according to the fitted quadratic Langevin model (see methods below). The Bal31 exonuclease digested almost all (~90%) of the 54 bp of the

TABLE 1

Back-calculated dielectric constant and refractive index of the biopolymer shell layer of the Au-DNA nanoconjugate based on the experimental results of SPR wavelength. For the first set of calculated λ, and n, the dielectric constant of Au is provided by Johnson and Christy (1972) Phys. Rev. B 6: 4370-4379, and the approximation equation* by Mulvaney (1996) Langmuir 12: 788-800, was used in calculations. For the second set of calculated λ, and n, the dielectric constant of Au was also provided by Johnson and Christy (supra), and the simulation code derived from BHCOAT (Bohren and Huffman (1983) Absorption and scattering of light by small particles. (John Wiley & Sons, Inc., New York) was used. For the third set of calculated λ and n, the dielectric constant was provided by Weaver et al. (1981) Optical properties of metals (Fachinformationszentrum, Karlsruhe, Germany), and the approximation equation by Mulvaney (supra) was used in calculations.

| | | | | Johnson & Christy polycrystalline Au | | Bohren & Huffman coated Au particle | | Weaver et al single crystalline Au | |
|---|---|---|---|---|---|---|---|---|---|
| Sample | Base Pair | Shell Thickness [nm] | SPR wavelength [nm] | Dielectric constant $\in (n^2)$ | Refractive index n | Dielectric constant $\in (n^2)$ | Refractive index n | Dielectric constant $\in (n^2)$ | Refractive index n |
| Au-Ph-DNA | 54 | 20.36 | 607 | 5.3467 | 2.3123 | 4.41 | 2.1 | 3.8552 | 1.9635 |
| +KpnI | 48 | 18.32 | 600 | 5.0315 | 2.2431 | 4.2025 | 2.05 | 3.6996 | 1.9234 |
| +SalI | 36 | 14.24 | 582 | 4.2382 | 2.0587 | 3.61 | 1.9 | 3.3078 | 1.8187 |
| +XhoI | 24 | 10.16 | 565 | 3.5108 | 1.8737 | 3.0625 | 1.75 | 2.9487 | 1.7172 |
| +HinDIII | 12 | 6.08 | 548 | 2.8053 | 1.6749 | 2.6244 | 1.62 | 2.6002 | 1.6125 |
| Au-Ph | 0 | 2 | 542 | 2.56 | 1.6 | 2.56 | 1.6 | 2.4798 | 1.5747 |

*$\lambda = \lambda_p^2 (\in^\infty + 2 \in_m)$, where λ is the wavelength, $\lambda_p$ is the bulk plasma wavelength of Au, $\in^\infty$ is the dielectric constant of Au at ultrahigh frequency, and $\in_m$ is the dielectric constant of the shell layer.

Figure 5D:
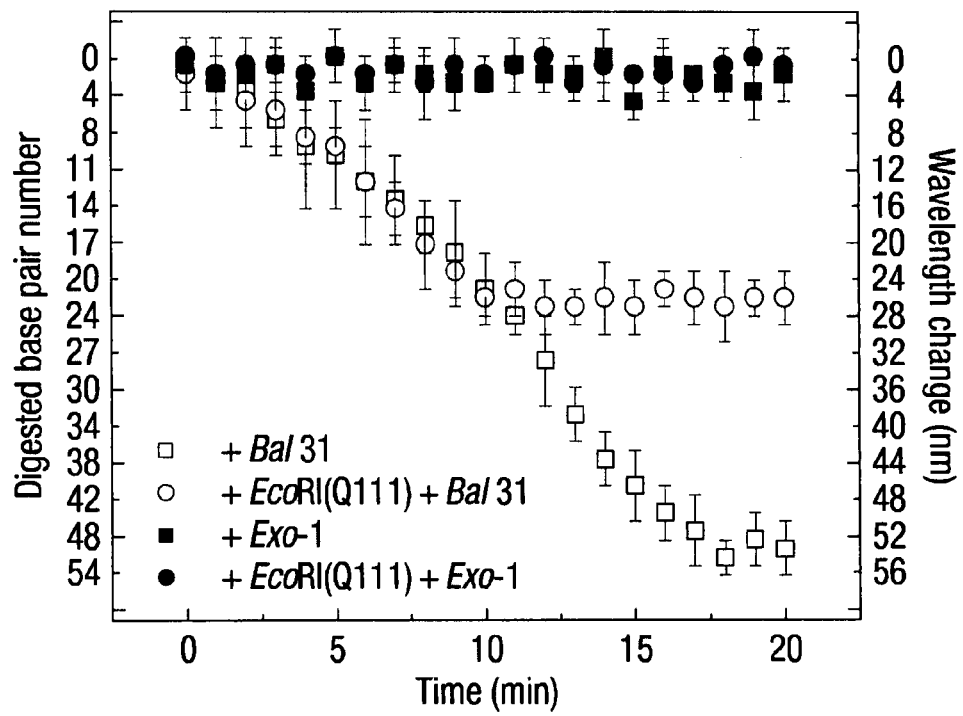

The relationship between the dsDNA length and the equivalent refractive index showed a good agreement with the quadratic Langevin model (Mazur and Jernigan, (1991) *Biopolymers* 31: 1615-1629) (fitted curve in FIG. 4B). An average wavelength shift of 1.24 nm bp (Parak et al. (2003) *Nano Lett.* 3: 33-36) was observed. Note that the full length of dsDNA, but it digested only ~25 bp with the EcoRI(Q111) blocking procession of Bal31 exonuclease. The stalling point of the exonuclease is around 25±3 bp from the distal end of the DNA, which is approximately 7 bp from the GAATTC site, and is in perfect agreement with previous measurements using conventional radiolabels (7±3 bp) (Pavco and Steege (1990) *Biol. Chem.* 265: 9960-9969). Previous mapping indicates that EcoRI(Q111) binds to 3 bp of dsDNA flanking the 3' boundary of the GAATTC sequence, and the steric exclusion between EcoRI(Q111) and exonuclease contributes to the other 4 bp. A control exonuclease, Exo-1, which does not cleave dsDNA, showed no effect on the ruler spectra (FIG. 5D).

The magnitudes of plasmon resonance shifts in our experiments are greater than previous reports on other biochemical reactions such as protein binding. We attribute the relatively larger wavelength shift to the stiffness of dsDNA axially and the unique dependence of its dielectric constant on its length. Additionally, the proteins and DNA have distinct electron densities, and it seems that the DNA scattering potential is one order of magnitude higher than that of the proteins. Therefore, the partial shortening or extension of the dsDNA will lead to a proportionally larger change around the Au surface compared with the change induced by a coiled protein binding or disassociation event. Furthermore, the DNA length shortening is also accompanied by a considerable decrease of DNA refractive index (Table 1, supra). An independent study by Doron-Mor and colleagues showed coordination-based self-assembled multilayers can offer thickness tuning of Au nanoparticle SPR spectra in the range 1-15 nm (Doron-Mor et al. (2005) *Chem. Eur. I.* 11: 5555-5562; Wanunu et al. (2005) *Am. Chem. Soc.* 127: 17877-17887), further validating our observation that nanoplasmonic spectra shift can be correlated with DNA length. The irregularity in the size and shape of the Au nanoparticles is possibly a contributing factor in the broadening of the spectra, and the resulting standard deviation. The accuracy and spectral resolution of our measurements can be further improved by using nanoparticles with better shape and size controls.

The time resolution of the nanoplasmonic molecular ruler can be as high as one spectrum per second by taking advantage of the high quantum efficiency of Rayleigh scattering compared with fluorescence or Raman scattering; therefore biomolecular reactions in the timescale of seconds can also be measured. Although only a simple dsDNA substrate is used here, there is no limit to the sequences or structure of the oligonucleotide substrates. The ability to resolve a single nanoparticle without the need for radioactive or fluorescent labeling also makes it possible to perform high-throughput screening in a high-density microarray or in microfluidic devices. The technology can also be used for the detection of other enzymes that induce length changes.

Methods

Synthesis of DNA Oligonucleotides and Preparation of Thiolated, FITC Labeled dsDNA.

Figure 6:
FIG. 6 illustrates cleavage of DNA with endonucleases. Test digestions of the 54 bp dsDNA with restriction endonucleases HindIII, KpnI, XhoI, and SalI were performed according to the manufacturer's instructions (New England Biolab, Beverly, Mass.). The cleavage sites for the various enzymes are shown in FIG. 1B. Appropriate amounts of buffer and water were mixed along with 1 µL of each of the enzyme in 100 µL final reaction volume. The reaction was incubated overnight at 37° C. The digestion was then verified by gel electrophoresis here on 5% NuSieve agarose gel in 1×TBE, with a 10 bp ladder as a molecular weight standard (Invitrogen, Carlsbad, Calif.). Note that the DNA shown in the gel is not tethered onto Au nanoparticles.

Two complementing strands of DNA, each 54 nucleotides long, were synthesized (Operon, Alameda, Calif.). They are (1) the oligonucleotide SprAuFor with dual thiol modification at the 5' end of the oligonucleotide (di-thiol-5'-AAA GGA TCC AAG CTT GAA TTC CTC GAG AGA TCT GTC GAC GAT CTC GGT ACC AAA-3', SEQ ID NO:16), and (2) the reverse complementing strand named SprAuRev (FITC-5'-TTT CCT AGG TTC GAA CTT AAG GA-GCT CTC TAG ACA GCT GCT ATA GCC ATG GTT T-3', SEQ ID NO:17). For the preparation of double-stranded DNA, 5'-thiolated SprAuFor was mixed at 1:1 molar ratio with of 5'-FITC-labeled SprAuRev, in a final volume of 100 µL. The mixture was first denatured by heating to 95° C. for 10 minutes, then the DNA strands were reannealed by cooling down slowly to room temperature. The quality of the DNA was checked by gel electrophoresis. Test digestion of DNA with restriction endonucleases HinDIII, KpnI, XhoI, and SalI were performed according to the manufacturer's instructions (New England Biolab, Beverly, Mass.) (FIG. 6). The cleavage sites for the various enzymes are shown (FIG. 1B). Appropriate amounts of buffer and water were mixed along with 1 µL of each of the enzyme in 100 µL final reaction volume. The reaction was incubated overnight at 37° C. The digestion was then verified by gel electrophoresis on 5% NuSieve agarose gel in 1×TBE, with a 10 bp ladder as a molecular weight standard (Invitrogen, Carlsbad, Calif.) (FIG. 6).

Solubilization of Au Nanoparticles with Phosphine Surfactants

In order to increase the stability of the Au nanoparticles for further manipulation, the surface capping of the 20 nm Au colloids (Ted Pella, Inc., Redding, Calif.) has been modified with a phosphine moiety (Bis(p-sulfonatophenyl)phenylphosphine, STREM Chemicals, Newburyport, Mass.) to solubilize 20 nm gold nanocrystals (Ted Pella, Inc, Redding, Calif.) as described previously with slight modifications (Parak et al. (2003) *Nano Lett.* 3: 33-36). 10 mL of 20 nm nanoparticle solution (2.32 nM) was concentrated by a factor of 200, bp precipitating the nanoparticles using an ultracentrifuge (14,000 RPM for 20 min). The pellet was resuspended in 50 µL of phosphine buffer (0.3 µM-4 mM phosphine in DEPC-treated water). The mixture was left overnight on a rocking platform at room temperature to allow sufficient time for surfactant exchange. The final concentration of the phosphine-coated gold particles was ~0.46 µM. We have run the gold nanoparticles on a 1% agarose gel, and observed the successful surfactant exchange. It was observed that 1 µL of the concentrated phosphine-coated gold particle was sufficient for the visualization of the Au nanoparticles in the gel.

Preparation of dsDNA-Conjugated Au Nanoparticle.

The dsDNA (FIG. 1B) was mixed with the concentrated phosphine-coated Au nanoparticles (see FIG. 7) in a molar ratio of 200:1, 100:1, 50:1 and 20:1, at room temperature for about 12 h, then stored at −20° C. Electrophoresis was used to verify the DNA attachment (FIG. 2B, panel a). The decreased mobility of the DNA-conjugated gold particles was clearly observed, indicating the successful DNA attachment to the gold nanoparticles. The presence of DNA can be confirmed by TEM imaging, with or without uranyl acetate staining, and the extra stain further increased the effective diameter of the whole complex (FIG. 2A).

Scattering Imaging and Spectroscopy of Single Au-DNA Nanoconjugates

The microscopy system consisted of a Carl Zeiss Axiovert 200 inverted microscope (Carl Zeiss) equipped with a dark-field condenser (1.2, (numerical aperture), 1.4), a true-color digital camera (CoolSNAPcf, Roper Scientific) and a 300 mm focal length and 300 grooves per mm monochromator (Acton Research) with a 1024×256 pixel cooled spectrograph CCD camera (Roper Scientific). A 2-µm-wide aperture was placed in front of the entrance slit of the monochromator to keep only a single nanoparticle in the region of interest. After photobleaching the fluorescence, the true-color scattering images of Au-DNA nanoconjugates were taken using a ×60 objective lens (numerical aperture=0.8) and the true-color camera with a white light illumination from a 100 W halogen lamp. The scattering spectra of Au-DNA nanoconjugates were routed to the monochromator and spectrograph CCD. Raw spectra were normalized with respect to the spectrum of a nonresonant nanoparticle (polystyrene) after background subtraction. In the real-time spectroscopy experiments, the nanoparticle-immobilized glass slide was mounted on a transparent indium tin oxide (ITO) heater with an external thermostat and heated to 37° C. or 25° C. The immobilized nanoparticles were immersed in a drop of buffer solution, which also served as the contact fluid for the dark-field condenser. The endonuclease or exonuclease enzymes with buffer solution were loaded by pipette into the contact fluid and the continuous spectrum acquisition started simultaneously. The microscopy system was completely covered by a dark shield, which prevented ambient light interference and excessive evaporation.

Cleavage Reaction of dsDNA on Au-DNA Nanoparticle Conjugate

We immobilized the Au-DNA nanoconjugates electrostatically on an ultraclean thin glass slide. The cleavage reaction for DNA was performed with endonucleases HindIII, KpnI, XhoI and SalI (FIG. 2B, panel b) and 1 µl of the Au-DNA particle in 100 µl final volume (3.5 nM final concentration for the endonucleases), as described above (FIG. 6), with only the modification of removing the reducing reagent from the reaction buffer and the enzymes in order to avoid detachment of the thiolated DNA from the gold nanoparticle.

Validation of Endonuclease Cleavage by Fluorescence Imaging

In order to confirm that the plasmon resonance frequency shift of the Au-DNA nanoconjugate is due to the effect of the endonuclease, and that the nanoplasmonic shift can accurately reflect DNA cleavage-induced size change, we compared the dark-field images (FIG. 3A, panels b-c) and FITC fluorescence images (FIG. 8, panels 2, and 3) of the Au-DNA nanoconjugates with nuclease to those of the Au-DNA nanoconjugates without nuclease (FIG. 3A, panels 1 and FIG. 8, panel 1). After 1-hour (FIG. 3A, panel b, and FIG. 8, panel 2) and 16-hour XhoI endonuclease reactions (FIG. 3A, panel c and FIG. 8, panel 3). The fluorescence in the Au-DNA nanoconjugates was strong before cleavage. Note the full length of the complete dsDNA (~20 nm) is much longer than the effective Forster transfer distance (<10 nm), and thus the FITC fluorophore was not quenched. The FITC fluorophore was detached from the Au nanoparticles and diffused into the buffer solution after the DNA cleavage, so that the overall fluorescence intensity at the image plane (where the Au nanoparticles are) decreased dramatically. The purpose of the FITC label removal experiment was solely for the validation of the enzymatic cleavage. The fluorescent label had no influence on the plasmon resonance measurement. The scattering spectra of the nanoconjugates were measured after the fluorescence was photobleached. In the first 3 minutes, there were a temporary red shift of the plasmon resonance wavelength, an increase of scattering intensity, and a flattening of the spectra. The brief oscillation is likely due to the initial loading of the enzyme molecules onto the dsDNA before incision.

Real-Time Measurement of Endonuclease Activity, Kinetics and Inhibition

For kinetic measurements, XhoI was used as the model enzyme. The cleavage was also confirmed by FITC fluorescence images (see, e.g., FIG. 8). The purpose of the FITC label removal experiment was solely for the validation of the enzymatic cleavage. The Au-DNA nanoconjugates were illuminated with a white light source for 20 min to completely photobleach the fluorescence prior to the spectroscopic measurement. The fluorescent label had no influence on the plasmon resonance measurement. The continuous acquisition of the scattering spectrum of a selected nanoparticle starts in synchronization with the introduction of the XhoI. For real-time kinetics measurement, one spectrum with 10 s integration time was acquired every minute. Significant blue shifts of the plasmon resonance wavelength were observed for the first 10 min and correlated with intensity decrease (FIG. 3B).

The rate of the endonuclease reaction on the Au-DNA nanoconjugate showed a concentration dependence, and was determined to followed a Michaelis-Menten enzyme kinetics (Mizu et al. (2004) *Biomaterials* 25: 3109-3116) (FIG. 3B). The rate constants were $5.8 \times 10^{-3}$ $s^{-1}$ (3.5 nM) and $1.5 \times 10^{-3}$ $s^{-1}$ (350 pM). The inhibition of the endonuclease reactions on the Au-DNA nanoconjugates was achieved with the simultaneous addition of 10 mM EDTA and the 3.5-nM XhoI enzymes; the $Mg^{2+}$ in the reaction buffer, which is required for XhoI activity, can be chelated by EDTA.

Bal-31 Footprinting of EcoRI(Q111) Bound on dsDNA-Au

The cleavage-defective EcoRI(Q111) was purified according to previous descriptions (King et al. (1989) *J. Biol. Chem.* 264: 11807-11815; Pavco et al. (1990) *J. Biol. Chem.* 265: 9960-9969; Jett and Bear (1994) *Proc. Natl. Acad. Sci., USA,* 91: 6870-6874), and incubated at 100 nM final concentration with the immobilized Au-DNA nanoconjugates (in this experiment, the FITC moiety was not used, so that exonuclease cleavage would not be affected) for 10 min in the 80 µl reaction buffer at 37° C. Next, 20 µl Bal31 enzymes (Clontech) was added into the reaction buffer containing immobilized Au-DNA nanoconjugates in 100 µl final volume, with a Bal31 final concentration of 100 nM. The binding buffer contained 50 mM NaCl, 10 mM $MgCl_2$, 0.025% Triton X-100 and 100 mM Tris-HCl pH 7.5 at 25° C.

Estimate of Diffusion Rate

The DNA cleavage we observed is not a diffusion-limited process. The diffusion rate of the endonuclease enzymes (number of enzyme molecules diffusing onto single nanoconjugates per unit time) can be estimated as $\Delta N/\Delta t = 4\pi DrC$, where $D=5 \times 10^{-7}$ $cm^2/sec$ is the diffusion constant of enzyme in water, $r=28$ nm is the radius of a single nanoconjugate, and $C=3.5$ nM is the molar concentration of enzymes. The diffusion rate is estimated to be 37 molecule/sec. Therefore the DNA digestion we observed is not a diffusion-limited process (otherwise the digestion of ~100 dsDNA on a single nanoconjugate would finish in a few seconds). On the other hand, the rate constant of the nuclease reaction on the nanoconjugate ($5.8 \times 10^{-3}$ $s^{-1}$ for higher concentrations of XhoI) is comparable to that in free solutions (Frye and Royer (1997) *Biophys. J.* 72: Th399-Th399). This implies that the Au nanoparticle has minimal impact on the enzyme activity and serves only as a highly sensitive sensor.

Calculation of the Refractive Index of dsDNA in Different Lengths.

The plasmon resonance wavelength of the Au-DNA nanoconjugate can be calculated using the Mie scattering theory. The pertinent variables include the dielectric constant of Au and the effective thickness and refractive index of the biopolymer shell (phosphine+dsDNA). We used the dielectric constant of Au at various wavelengths provided by Johnson and Christy (1972) *Phys. Rev. B* 6: 4370-4379, though their results are considered more appropriate for bulk or polycrystalline Au. We estimated the thickness of the phosphine layer to be 2 nm. The length of the dsDNA is calculated as 0.34 nm/bp. The length of the dsDNA, before cleavage and after cleavage by KpnI, SalI, XhoI, and HinDIII, are respectively 54, 48, 36, 24, 12, and 0 bp, and therefore the biopolymer shell thickness are 18.36, 16.32, 12.24, 8.16, 4.08, and 2 nm, respectively. Using the calculation program for coated particle by Bohren and Huffman (1983) *Absorption and scattering of light by small particles*. (John Wiley & Sons, Inc., New York), the dielectric constants of the biopolymer shell in different thickness are found by way of trial and error. The equivalent refractive index can be considered to be simply the square root of the dielectric constant. The dependence of the dielectric constant of dsDNA on its length has been studied and the quadratic Langevin model to describe the relationship has been established (Mazur and Jernigan (1991) *Biopolymers* 31: 1615-1629). We fitted the calculated refractive index according to the following empirical formula $\in(l)=n^2(l)=a[\text{Coth}(bl^2)-1/bl^2]+c$, where a, b and c are three fitting variables (Bohren and Huffman, (1983) *Absorption and Scattering of Light by Small Particles* (Wiley, New York). Our calculation results agree with the results provided by Mulvaney (1996) *Langmuir* 12: 788-800, very well.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A nanoplasmon resonance ruler for calibrating nucleic acid length changes in a plasmon resonance system, said ruler comprising:

a nanoparticle having a nucleic acid attached thereto to form a nanoparticle-nucleic acid conjugate, where said nucleic acid comprises at least a first restriction site and a second restriction site positioned such that the conjugates cleaved at the first restriction site provide plasmon resonance signatures that are distinguishable from the plasmon resonance signatures produced by the nucleic acid conjugates cleaved at second restriction site, and/or the intact conjugate, and wherein the nanoparticle surface is functionalized with a phosphine layer.

2. A nanoplasmon resonance ruler for calibrating nucleic acid length changes in a plasmon resonance system, said ruler comprising:

a nanoparticle having a nucleic acid attached thereto to form a nanoparticle-nucleic acid conjugate, where said nucleic acid comprises at least a first restriction site and a second restriction site positioned such that the conjugates cleaved at the first restriction site provide plasmon resonance signatures that are distinguishable from the plasmon resonance signatures produced by the nucleic acid conjugates cleaved at second restriction site, and/or the intact conjugate, and wherein the nanoparticle surface is silica coated and functionalized using aminosilane molecules.

3. A nanoplasmon resonance ruler for calibrating nucleic acid length changes in a plasmon resonance system, said ruler comprising:

a nanoparticle having a nucleic acid attached thereto to form a nanoparticle-nucleic acid conjugate, where said nucleic acid comprises at least a first restriction site and a second restriction site positioned such that the conjugates cleaved at the first restriction site provide plasmon resonance signatures that are distinguishable from the plasmon resonance signatures produced by the nucleic acid conjugates cleaved at second restriction site, and/or the intact conjugate, and wherein the conjugate comprises from about 10 to about 10,000 nucleic acid molecules per nanoparticle.

4. A nanoplasmon resonance ruler for calibrating nucleic acid length changes in a plasmon resonance system, said ruler comprising:

a nanoparticle having a nucleic acid attached thereto to form a nanoparticle-nucleic acid conjugate, where said nucleic acid comprises at least a first restriction site and a second restriction site positioned such that the conjugates cleaved at the first restriction site provide plasmon resonance signatures that are distinguishable from the plasmon resonance signatures produced by the nucleic acid conjugates cleaved at second restriction site, and/or the intact conjugate, and wherein the conjugate is immobilized on a substrate appropriate for surface plasmon resonance.

5. A nanoplasmon resonance ruler for calibrating nucleic acid length changes in a plasmon resonance system, said ruler comprising:

a nanoparticle having a nucleic acid attached thereto to form a nanoparticle-nucleic acid conjugate, where said nucleic acid comprises at least a first restriction site and a second restriction site positioned such that the conjugates at the first restriction site provide plasmon resonance signatures that are distinguishable from the plasmon resonance signatures produced by the nucleic acid conjugates cleaved at second restriction site, and/or the intact conjugate, and wherein the conjugate is electrostatically immobilized on a glass, quartz, or ceramic surface.

6. The nanoplasmon resonance ruler according to any one of claims 1, 2, 3, 4, and 5, wherein said nucleic acid is a double-stranded DNA, or a double-stranded RNA.

7. The nanoplasmon ruler of claim 6, wherein said nucleic acid is a double-stranded nucleic acid comprising a first strand attached to said nanoparticle and a second strand hybridized to said first strand, but not otherwise attached to said nanoparticle.

8. The nanoplasmon resonance ruler according to any one of claims 1, 2, 3, 4, and 5, wherein said nucleic acid comprises at least three different restriction sites.

9. The nanoplasmon resonance ruler according to any one of claims 1, 2, 3, 4, and 5, wherein said nucleic acid further comprises a protein binding site.

10. The nanoplasmon resonance ruler according to any one of claims 1, 2, 3, 4, and 5, wherein said nucleic acid ranges in length from 3 nucleotides to about 500 nucleotides.

11. The nanoplasmon resonance ruler according to any one of claims 1, 2, 3, 4, and 5, wherein the nanoparticle is selected from the group consisting of a nanosphere, a nanocrescent, a nanowire, a nanohorn, a nanotube, a nanopyramid, a nanorod, a nanotetrepod, a single- or multi-layered nanodisk, and a nanohorn.

12. The nanoplasmon resonance ruler according to any one of claims 1, 2, 3, 4, and 5, wherein the nanoparticle comprises a metal or semiconductor material.

13. The nanoplasmon resonance ruler according to any one of claims 1, 2, 3, 4, and 5, wherein the nanoparticle comprises a material selected from the group consisting of a noble metal, a noble metal alloy, a noble metal composite.

14. The nanoplasmon resonance ruler according to any one of claims 1, 2, 3, 4, and 5, wherein the nanoparticle comprises a material selected from the group consisting of gold, gold alloy, silver, silver alloy, copper, copper alloy, platinum, platinum alloy, CdSe semiconductor, CdS semiconductor, CdSe coated with ZnS, magnetic colloidal materials, ZnS, ZnO, $TiO_2$, AgI, AgBr, $HgI_2$, PbS, PbSe, ZnTe, CdTe, $In_2S3$, $In_2Se_3$, $Cd_3P_2$, $Cd_3As_2$, InAs, and GaAs.

15. The nanoplasmon resonance ruler according to any one of claims 1, 2, 3, 4, and 5, wherein the nanoparticle material comprises silver.

16. The nanoplasmon resonance ruler according to any one of claims 1, 2, 3, 4, and 5, wherein the nanoparticle material comprises gold.

17. The nanoplasmon resonance ruler according to any one of claims 1, 2, 3, 4, and 5, wherein the nanoparticle size ranges from about 5 nm to about 150 nm.

* * * * *